United States Patent [19]

Veber et al.

[11] 4,161,521
[45] Jul. 17, 1979

[54] SOMATOSTATIN ANALOGS

[75] Inventors: Daniel F. Veber, Ambler; Frederick W. Holly, Glenside; Robert G. Strachan, Warrington; William J. Paleveda, Lansdale; Ruth F. Nutt, Green Lane; Ralph F. Hirschmann, Blue Bell, all of Pa.

[73] Assignee: Merck & Co., Inc., Rahway, N.J.

[21] Appl. No.: 695,348

[22] Filed: Jun. 14, 1976

Related U.S. Application Data

[63] Continuation-in-part of Ser. No. 680,005, Apr. 23, 1976, abandoned, which is a continuation-in-part of Ser. No. 603,067, Aug. 8, 1975, abandoned.

[51] Int. Cl.$^2$ .................... A61K 37/00; C07C 103/52
[52] U.S. Cl. .............................. 424/177; 260/112.5 S
[58] Field of Search .................. 260/112.5 S; 424/177

[56] References Cited

U.S. PATENT DOCUMENTS

| | | | |
|---|---|---|---|
| 3,842,066 | 10/1974 | McKinley et al. | 260/112.5 S |
| 3,904,594 | 9/1975 | Guillemin et al. | 260/112.5 S |
| 3,988,304 | 10/1976 | Garsky | 260/112.5 S |

OTHER PUBLICATIONS

J. Med. Chem. 18, 123 (1975).
Endocrinology 98, 336 (1976).
Biochem. Biophys. Res. Commun. 65, 746 (1975).
Coll. Czech. Chem. Commun. 32, 1229 (1967).
Experientia 20, 570 (1964).
J.A.C.S. 98, 2367 (1967).

Primary Examiner—Delbert R. Phillips
Attorney, Agent, or Firm—Walter Patton; Harry E. Westlake, Jr.

[57] ABSTRACT

Somatostatin analogs having the structural formula:

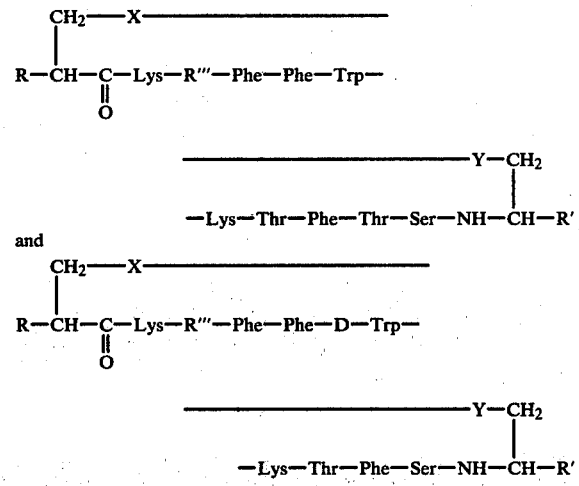

and are prepared by controlled stepwise procedures starting with individual amino acid components. These peptides have the property of lowering blood glucose, inhibiting gastric secretion, inhibiting growth hormone release and inhibiting glucagon release in humans and animals.

37 Claims, No Drawings

SOMATOSTATIN ANALOGS

This application is a continuation-in-part of application Ser. No. 680,005, filed Apr. 23, 1976, abandoned which in turn is a continuation-in-part of co-pending application Ser. No. 603,067, filed Aug. 8, 1975, abandoned.

BACKGROUND OF THE INVENTION

Somatostatin is a tetradecapeptide having the structure:

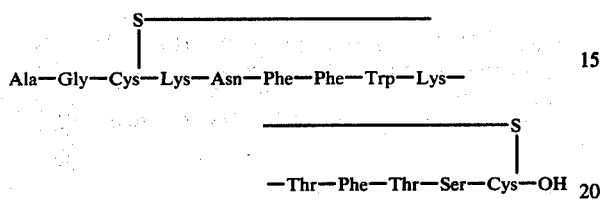

and is known to inhibit the release of growth hormone. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself. The present invention provides somatostatin analogs having the biological activity of somatostatin and a longer duration of action and a novel method for preparing said analogs.

SUMMARY OF THE INVENTION

This invention is concerned with novel somatostatin analogs having a longer activity than naturally occurring somatostatin and having the structural formula:

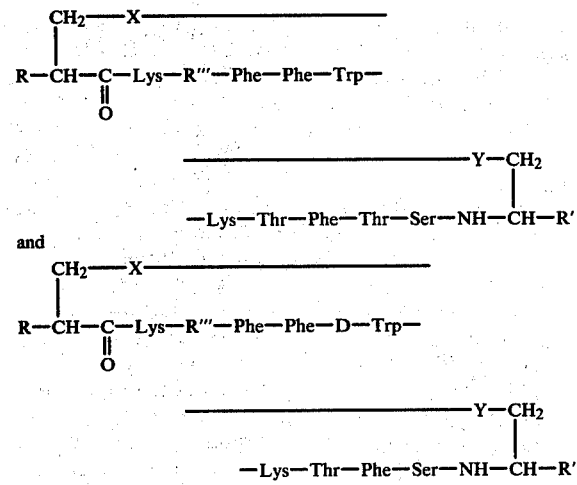

wherein:
X is $CH_2$, S,

$SO_2$ or $[X]_n$ wherein n=0;
Y is $CH_2$, S,

$SO_2$ or $[Y]_n$ wherein n=0;
R is H, $NH_2$ or R"NH wherein
R" is Ala—Gly—, lower acyl containing 2 to 6 carbon atoms or aroyl containing 7 to 21 carbon atoms;
R' is H or $CO_2H$; wherein X and Y are not both heteroatoms and R'" is asparagine, alanine or α-aminobutyric acid.

The somatostatin analogs of the present invention differ from somatostatin by virtue of the fact that the two adjacent heteroatoms of the disulfide bridge, —S—S—, of the cystine amino acid residue of somatostatin set forth in the following structural formula:

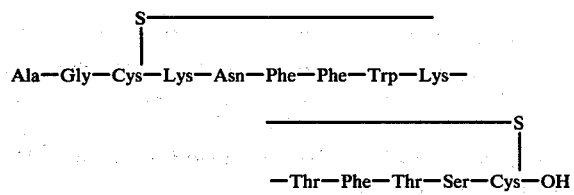

is deleted or replaced by the more stable groups containing C and S, such as:

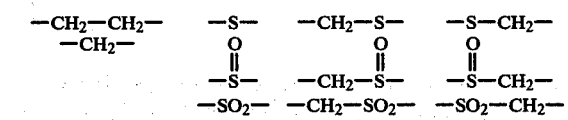

which contain no adjacent heteroatoms. The somatostatin analogs of the present invention include those wherein the Ala-Gly and amino group of $Cys^3$ of somatostatin is deleted and replaced by hydrogen; amino; a lower acylamino group, wherein the lower acyl group contains 2 to 6 carbon atoms such as acetylamino; or an aroylamino group, wherein the aroyl group contains from 7 to 21 carbon atoms such as benzoylamino and those wherein the C-terminal carboxylic acid group of cystine is replaced by hydrogen. Furthermore, the somatostatin analogs of the present invention include those wherein L-tryptophan, Trp, at the 8-position is replaced by D-tryptophan, D-Trp.

The preferred somatostatin analogs of the present invention are illustrated by the following structural formula:

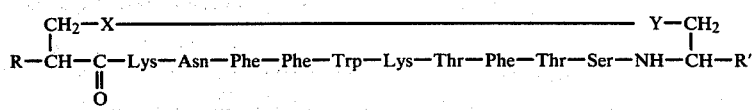

and

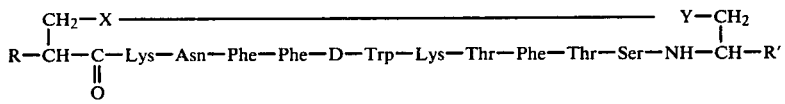

wherein:
X—Y is CH₂—CH₂, R is H, R' is H; or
X—Y is CH₂—CH₂, R is NH₂, R' is CO₂H; or
X—Y is CH₂—S, R is H and R' is CO₂H; or
X—Y is S—CH₂, R is H and R' is CO₂H.

In further preferred somatostatin analogs of the present invention, X—Y is CH₂—CH₂; R is hydrogen and R' is hydrogen or CO₂H. Accordingly, the structure of these further preferred somatostatin analogs are explicitly illustrated by the structural formulas;

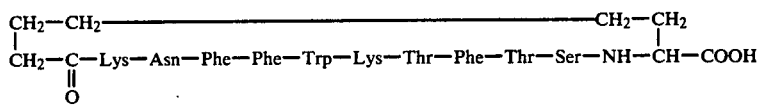

designated cyclo(ω-Asu-Lys-Asn-Phe-Phe-Trp-Lys-Thr-Phe-Thr-Ser) or des(Ala¹, Gly²)-desamino[Cys³-]dicarba³,¹⁴-somatostatin;

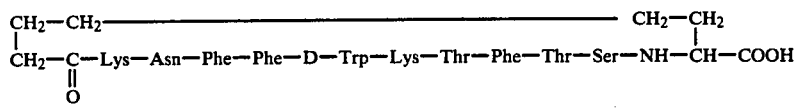

designated des(Ala¹, Gly²)-desamino[Cys³]dicarba³,¹⁴-[D-Trp⁸]-somatostatin;

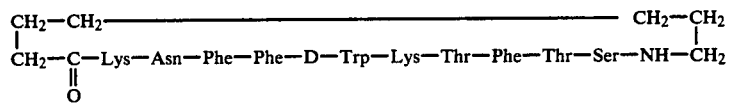

designated des(Ala¹, Gly²)-desamino[Cys³]descarboxy[Cys¹⁴]-dicarba³,¹⁴-[D-Trp⁸]-somatostatin.

The somatostatin analogs of the present invention differ from somatostatin by virtue of the fact that the component

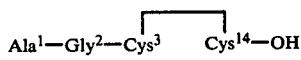

in somatostatin is deleted and replaced by the component:

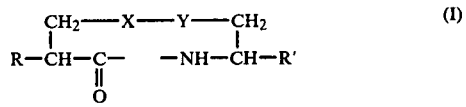

wherein X, Y, R and R' are as defined above. Those novel somatostatin analogs containing α-aminosuberic acid, such as des(Ala¹, Gly²)-desamino[Cys³]dicarba³,¹⁴-somatostatin; des(Ala¹, Gly²)-desamino[Cys³-]dicarba³,¹⁴-[D-Trp⁸]-somatostatin and des(Ala¹, Gly²)-desamino[Cys³]descarboxy[Cys¹⁴]dicarba³,¹⁴-[D-Trp⁸]-somatostatin have no N-terminal amino group, thus eliminating one of the groups involved in enzymatic cleavage of the molecule by aminopeptidases. Those somatostatin analogs containing ω-aminoheptanoic acid, such as, des(Ala¹, Gly²)-desamino[Cys³]descarboxy-[Cys¹⁴]dicarba³,¹⁴-somatostatin and des(Ala¹, Gly²)-desamino[Cys³]descarboxy[Cys¹⁴]dicarba³,¹⁴-[D-Trp⁸]-somatostatin lack a C-terminal carboxyl group, thus eliminating one of the groups involved in enzymatic cleavage of the molecule by carboxypeptidases. Furthermore, the replacement of the adjacent heteroatoms of the disulfide bridge of somatostatin with the group, —CH₂—CH₂—, —S—CH₂— or —CH₂—S— increases the stability of the analog in vivo by slowing down enzymatic degradation by reductive cleavage. Therefore, these analogs are more resistant to cleavage in vivo and thus have a prolonged duration of action.

This invention encompasses the following novel blocked peptide intermediates useful in the preparation of the somatostatin analogs of this invention:

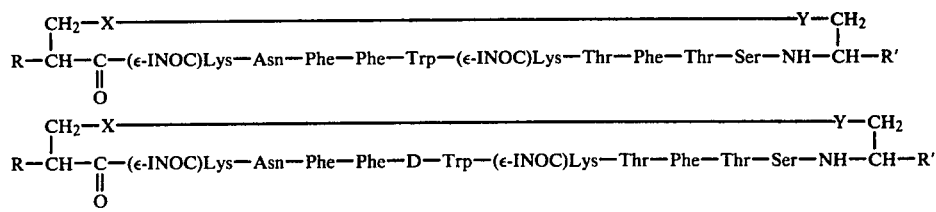

-continued

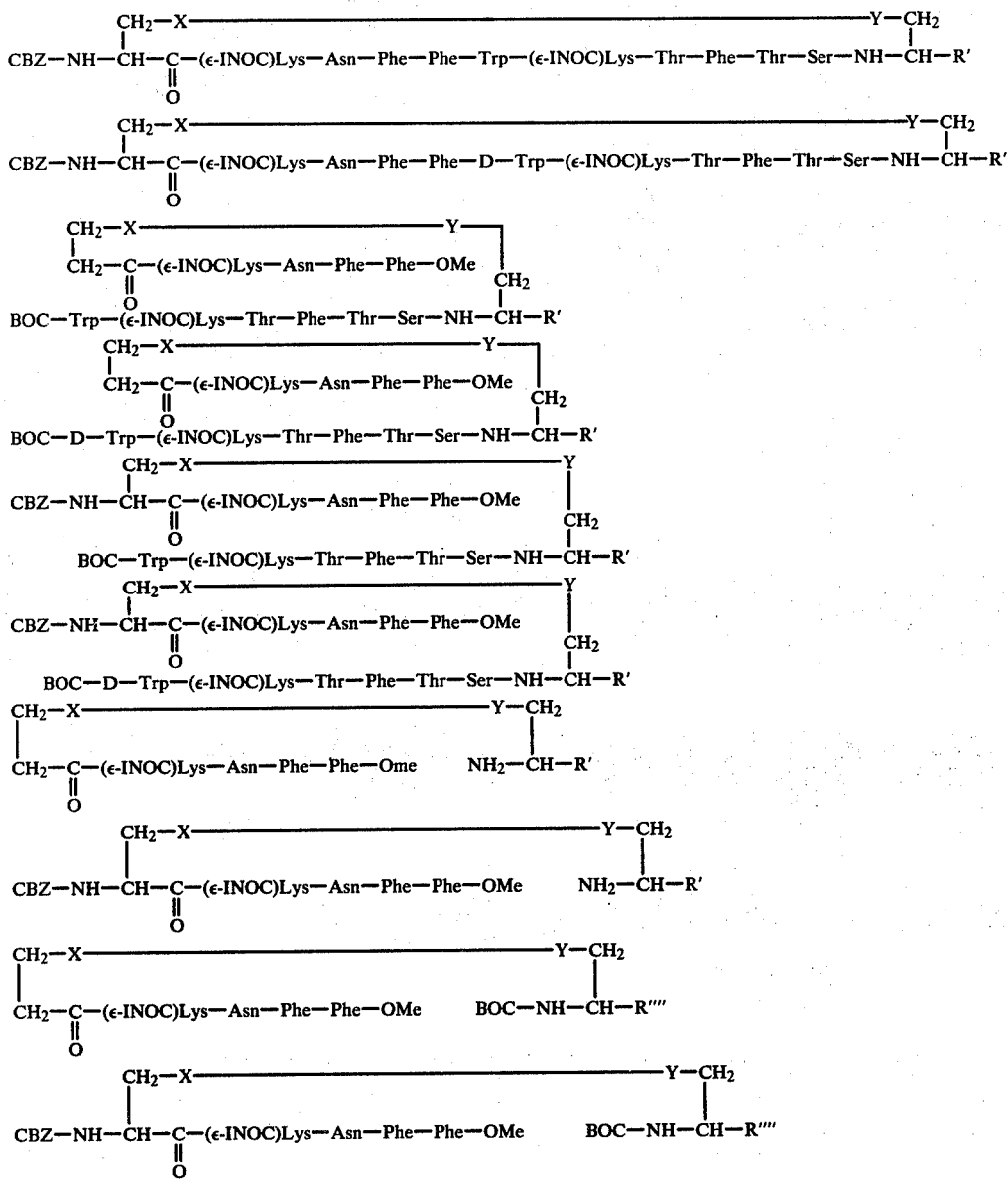

wherein X, Y, R and R' are as defined above and R'''' is H, or —COOtBu. All the abbreviations used herein are defined below.

The abbreviated designations, which are used herein for the amino acid components, certain preferred protecting groups, amino acid activation groups, condensing agents, reagents and solvents employed in the process of this invention are as follows:

| Abbreviated Designation | Amino Acid |
|---|---|
| Lys | L-lysine |
| Asn | L-asparagine |
| Phe | L-phenylalanine |
| Trp | L-tryptophan |
| D-Trp | D-tryptophan |
| Thr | L-threonine |
| Ser | L-serine |
| Asu | α-aminosuberic acid |

| Abbreviated Designation | Protecting Groups |
|---|---|
| INOC | isonicotinyloxycarbonyl |
| BOC | tert-butyloxycarbonyl |
| OMe | methyl ester |
| tBu | tert-butyl |
| CBZ | benzyloxycarbonyl |

| Abbreviated Designation | Activating Groups |
|---|---|
| NPE | p-nitrophenyl ester |
| HSE | N-hydroxysuccinimide ester |
| HBT | 1-hydroxybenzotriazole |

| Abbreviated Designation | Condensing Agents |
|---|---|
| DCCI | dicyclohexylcarbodiimide |

| Abbreviated Designation | Reagents |
|---|---|
| TFA | trifluoroacetic acid |
| TEA | triethylamine |
| DIPEA | diisopropylethylamine |

Abbreviated

| Designation | Solvents |
|---|---|
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

The novel somatostatin analogs of the present invention can be prepared, according to the process of this invention, by block synthesis, wherein various peptide segments of the somatostatin analog are individually synthesized, and these segments are then coupled in the desired sequence to the compounds (II) and (III) having the structural formulas:

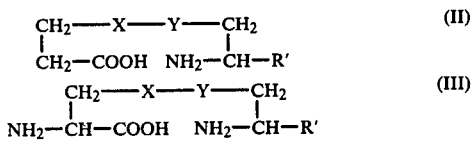

wherein X, Y and R' are as defined above to form the open-chained form of the desired product. The open-chained form of the product is ring closed and the protective groups removed, and when desired, the sulfide analog is oxidized to the sulfoxide or sulfone to obtain those analogs wherein —X—Y— contains an

or $SO_2$ group. In those cases wherein R is R"NH, the ring-closed intermediate is selectively deblocked to remove the protective group of the N-terminal amine only. The resulting N-terminal amine is condensed by suitable means with an R" group. The preferred overall procedure for the preparation of the somatostatin analogs of the present invention wherein X, Y and R' are as defined above and wherein R is H is outlined diagrammatically in Table 1. Table 1 indicates the preparation of L-tryptophan containing analogs; it is to be understood that analogs containing D-tryptophan can be prepared by the identical process set forth in Table 1 with the exception that L-tryptophan is replaced by D-tryptophan.

TABLE 1

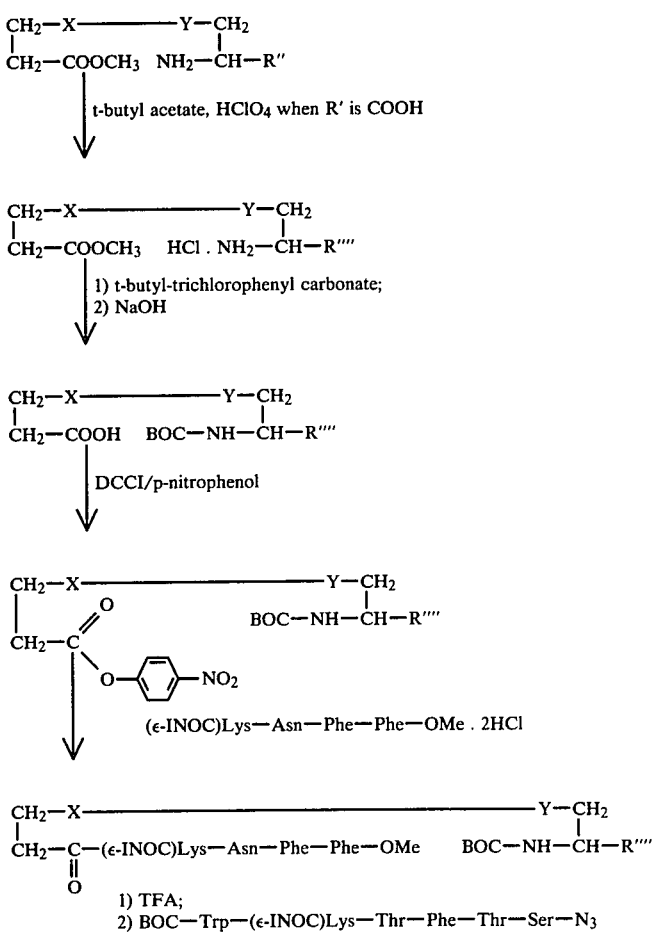

TABLE 1-continued

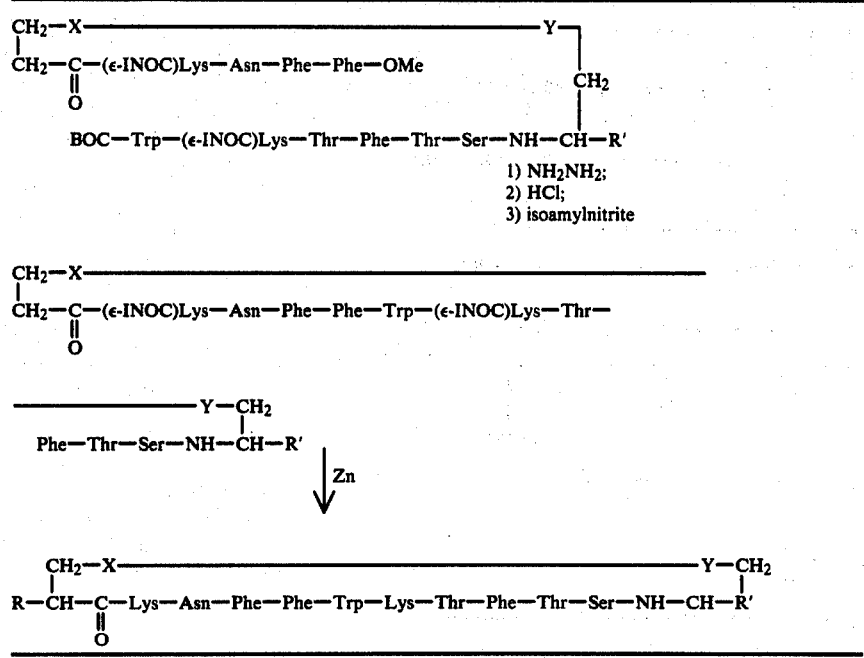

wherein X, Y and R' are as defined above, R is H, and R'''' is

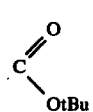

when R' is COOH and the amino acid Trp may be replaced by D-Trp.

In the case wherein the group, —X—Y—, contains the group, $$-\underset{\|}{\overset{O}{S}}-$$

or —$SO_2$—, a further oxidation step with a suitable oxidizing agent such as performic acid or hydrogen peroxide, respectively, is required.

The somatostatin analogs of the present invention wherein X, Y and R' are as defined above and wherein R is —$NH_2$ and R'' wherein R'' is as defined above are prepared by the process described in Table 2. Table 2 indicates the preparation of L-tryptophan containing analogs; it is to be understood that analogs containing D-tryptophan can be prepared by the identical process set forth in Table 2 with the exception that L-tryptophan is replaced by D-tryptophan.

TABLE 2

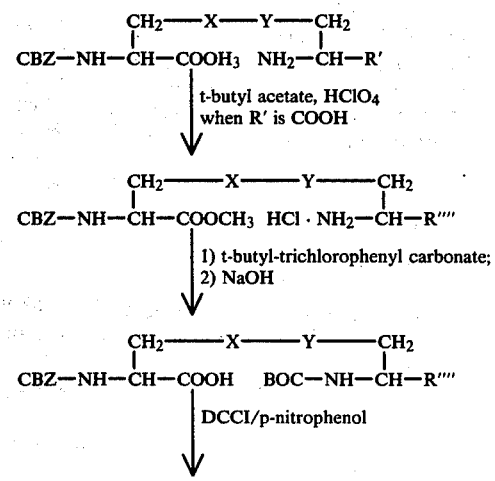

TABLE 2-continued

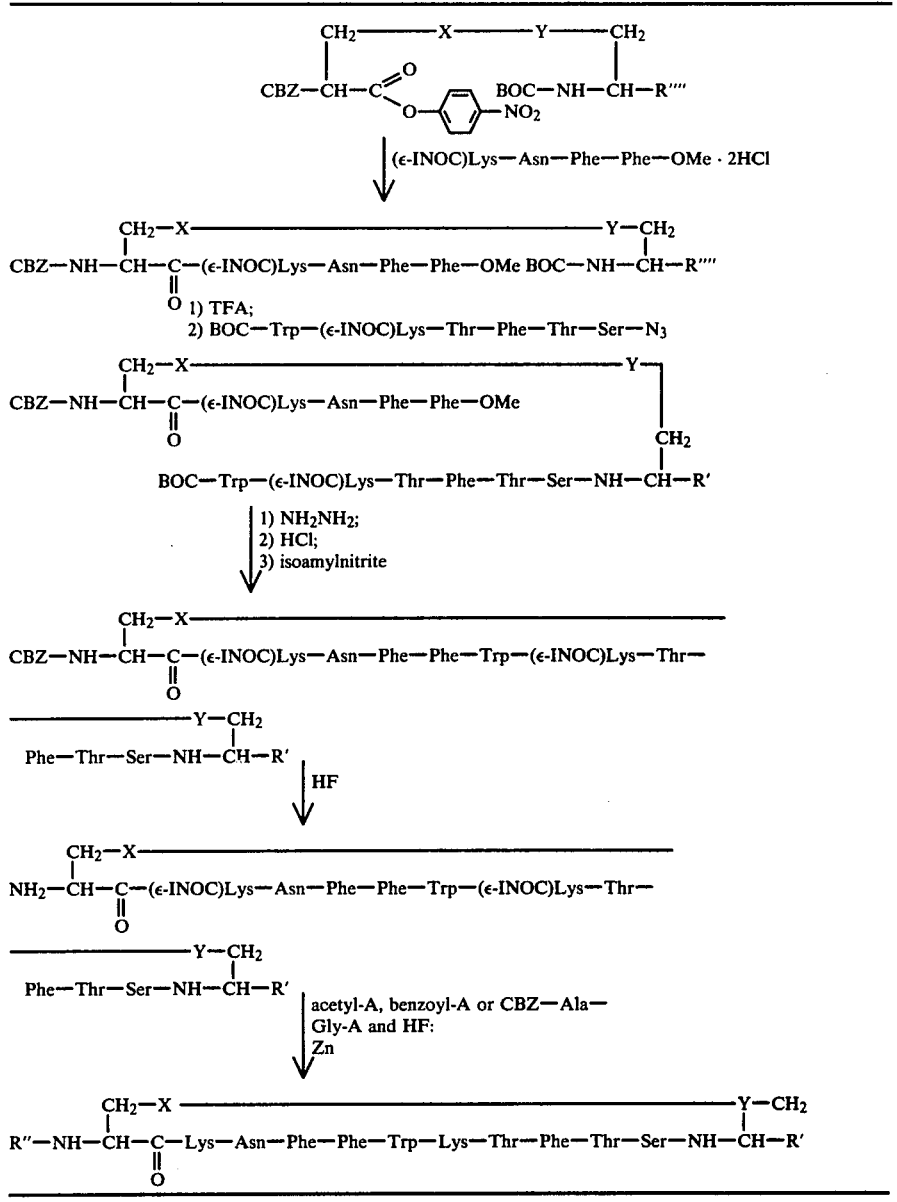

wherein X, Y, R', R" and R"" are as defined above; A is any suitable group known in the art for forming an amide bond such as halide, anhydride or active ester and the amino acid Trp may be replaced by D-Trp.

In the case wherein the group; —X—Y—, contains the group,

or —SO₂—, a further oxidation step with a suitable oxidizing agent such as performic acid or hydrogen peroxide, respectively, is required.

The starting material,

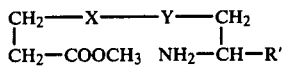

for the process set forth in Table 1 wherein R' is COOH and X—Y is —CH₂—S— or —S—CH₂— is described in the art as set forth in the references:

K. Jošt, Collect. Czech. Chem. Comm., 36, 223 (1971); and

K. Jošt and F. Sorm, Collect. Czech. Chem. Comm., 36, 238 (1971).

The starting material,

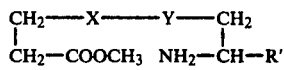

for the process set forth in Table 1 wherein R' is H and X-Y is —CH₂—CH₂— is described in the art as set forth in the reference:

C. F. Horn et al., Angew. Chem. 74, 531 (1962); Chemical Abstract Vol. 57; 11411(c).

The starting material,

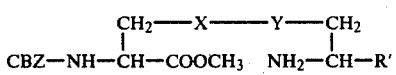

for the process set forth in Table 2 wherein R' is COOH and X—Y is —CH₂—S— and —S—CH₂— is described in the art as set forth in the references:

K. Jošt and F. Šorm, Collect. Czech. Chem. Comm., 36, 238 (1971); and

K. Jošt and J. Rudinger, Collect. Czech. Chem. Comm. 32, 2488 (1967).

which are herein incorporated by reference.

All the other necessary amino acid derivatives necessary for carrying out the invention as set forth in Tables 1 and 2 are also to be found in the prior art except for the case of the intermediate compound,

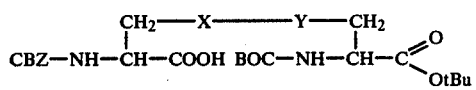

set forth in Table 2 wherein —X—Y— is —CH₂—CH₂—. This intermediate is prepared by the Kolbe electrolytic oxidative decarboxylation of two molecules of suitably blocked glutamic acid according to the scheme:

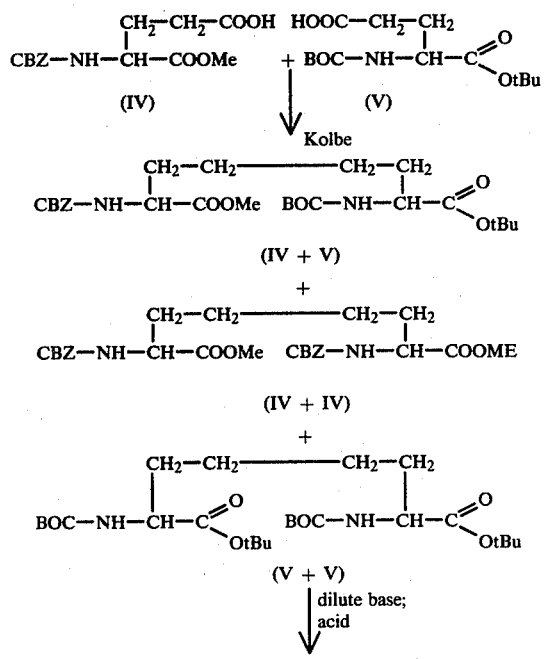

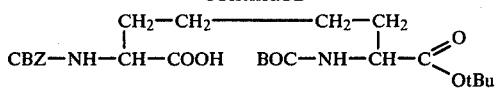

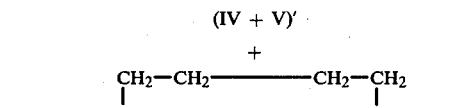

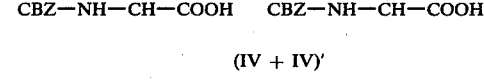

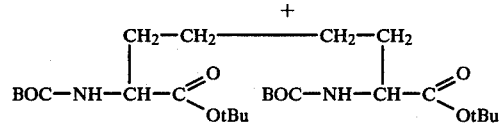

The desired monocarboxylic acid (IV+V)' is easily separated from the dicarboxylic acid (IV+IV)' and the neutral compound (V+V)' by methods well known in the art. The compound (IV+V)' is employed for the preparation of:

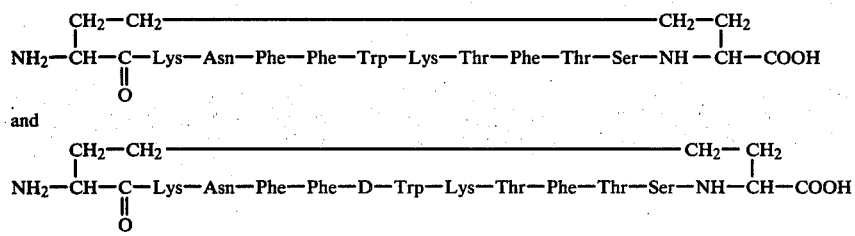

according to the process described in Table 2.

The peptide segments, (ε-INOC)Lys-Asn-Phe-Phe-OMe.2HCl; BOC-Trp-(ε-INOC)Lys-Thr-Phe-Thr-Ser-N₃ and BOC-D-Trp-(ε-INOC)Lys-Thr-Phe-Thr-Ser-N₃ illustrated in the process of Tables 1 and 2 are themselves conveniently prepared by sequential synthesis in solution using the HSE, NPE or HBT active ester procedure or the azide procedure.

In carrying out these sequential or block syntheses, involving reaction between carboxyl (or activated carboxyl) of one amino acid and amino group of the other, it is ordinarily preferred to protect the amino groups in the amino acid or peptide undergoing reaction at the carboxyl end of the molecule, as well as other functional groupings in both reactants reactive under the conditions of such syntheses. Protecting groups must retain their protecting properties under the peptide coupling conditions, and must be selectively removable without affecting peptide linkages. Protecting groups to be removed following a particular step must also be selectively removable without affecting other protecting groups to be retained in later coupling steps.

Amino-protecting groups ordinarily employed include acyl-type substituents such as formyl, phthalyl, trifluoroacetyl, toluenesulfonyl, dibenzylphosphoryl, nitrophenylsulfenyl, tritylsulfenyl, o-nitrophenoxyacetyl, and the like, urethane-type protecting substituents such as benzyloxycarbonyl (carbobenzoxy), p-methoxycarbobenzoxy, p-nitrocarbobenzoxy, t-butyloxycarbonyl, 2-(p-biphenylyl)-2-isopropyloxycarbonyl, isonicotinyloxycarbonyl, and the like, alkyl-type substituents such as triphenylmethyl, trialkylsilyl, trimethylsilyl, and the like. The group preferred for protecting the ε-amino group of lysine is isonicotinyloxycarbonyl. It is preferred to utilize tert-butyloxycarbonyl (BOC) for protecting the α-amino group in the amino acids (or peptides) undergoing reaction at the carboxyl end of the molecule, since the BOC protecting group is readily removed following such reaction and prior to the subsequent step (wherein such α-amino group itself undergoes reaction) by relatively mild action of acids (e.g. trifluoroacetic acid, or hydrogen chloride in ethyl acetate) which treatment does not substantially affect groupings, such as carbobenzoxy (CBZ) and isonicotinyloxycarbonyl, used to protect other amino groups such as the basic amino group of lysine. The carbobenzoxy group is removable by treatment with hydrogen bromide in glacial acetic acid or hydrogen fluoride, which treatment does not substantially affect the isonicotinyloxycarbonyl group. The removal with hydrogen fluoride is facilitated by the presence of anisole. The isonicotinyloxycarbonyl group is removable by the action of zinc.

Carboxyl-protecting groups ordinarily employed include amides, salt formation, ester substituents such as the methyl and ethyl esters (which are preferred where subsequent conversion, via the hydrazide, to the azide is desired), the benzyl ester, p-nitrobenzylester, t-butyl ester, and the like. Hydroxyl groups are ordinarily not protected in the synthesis of the somatostatin analogs of this invention where the coupling reactions are conducted in solution, although tetrahydropyranyl, benzyl, trifluoroacetyl, t-butyl, and the like, may be used for such protection if desired.

The selection of protecting groups is in part dictated by particular coupling conditions, in part by the amino acid and peptide components involved in the reaction.

Guides for selecting particular protecting groups to be employed herein are set forth in detail in the French Patent 1,496,536, and the protecting groups disclosed in that patent are incorporated herein by reference.

DESCRIPTION OF THE PREFERRED EMBODIMENTS

The preferred overall procedure for the preparation of the preferred somatostatin analogs of this invention, des(Ala$^1$, Gly$^2$)-desamino[Cys$^3$]dicarba$^{3,14}$-somatostatin and des(Ala$^1$, Gly$^2$)-desamino[Cys$^3$]dicarba$^{3,14}$-[D-Trp$^8$]-somatostatin, is outlined diagrammatically in Table 3. Table 3 indicates the preparation of an L-tryptophan containing analog; it is to be understood that the D-tryptophan containing analog can be prepared by the identical process set forth in Table 3 with the exception that BOC-L-tryptophan HSE is replaced by BOC-D-tryptophan HSE in Step 5a).

The other novel somatostatin analogs of the present invention are prepared by the process described below in Table 3 wherein the α-aminosuberic acid in the process described in Step 10 is replaced by the compounds having the structural formulas:

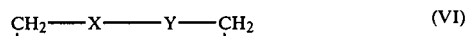
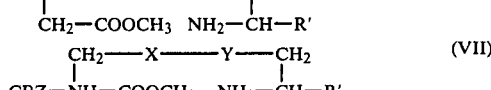

wherein X, Y and R' are as defined above and the conversions described in Steps 10 to 15 and 17 to 19 are carried out. However, in the case wherein R is R'', further steps are necessary to condense the N-terminal amine with an acetyl or benzoyl group or with CBZ-Ala-Gly. In the latter use, a further step to remove the protective group from the α-amino group of Ala is necessary. Furthermore, in the case wherein the group —X—Y— contains a sulfoxide group,

or —SO$_2$—, oxidation with a suitable oxidizing agent, such as performic acid or hydrogen peroxide, respectively, is required as an additional step. The corresponding D-tryptophan analogs can be prepared by replacing BOC-L-tryptophan HSE in Step 5a) with BOC-D-tryptophan HSE.

TABLE 3
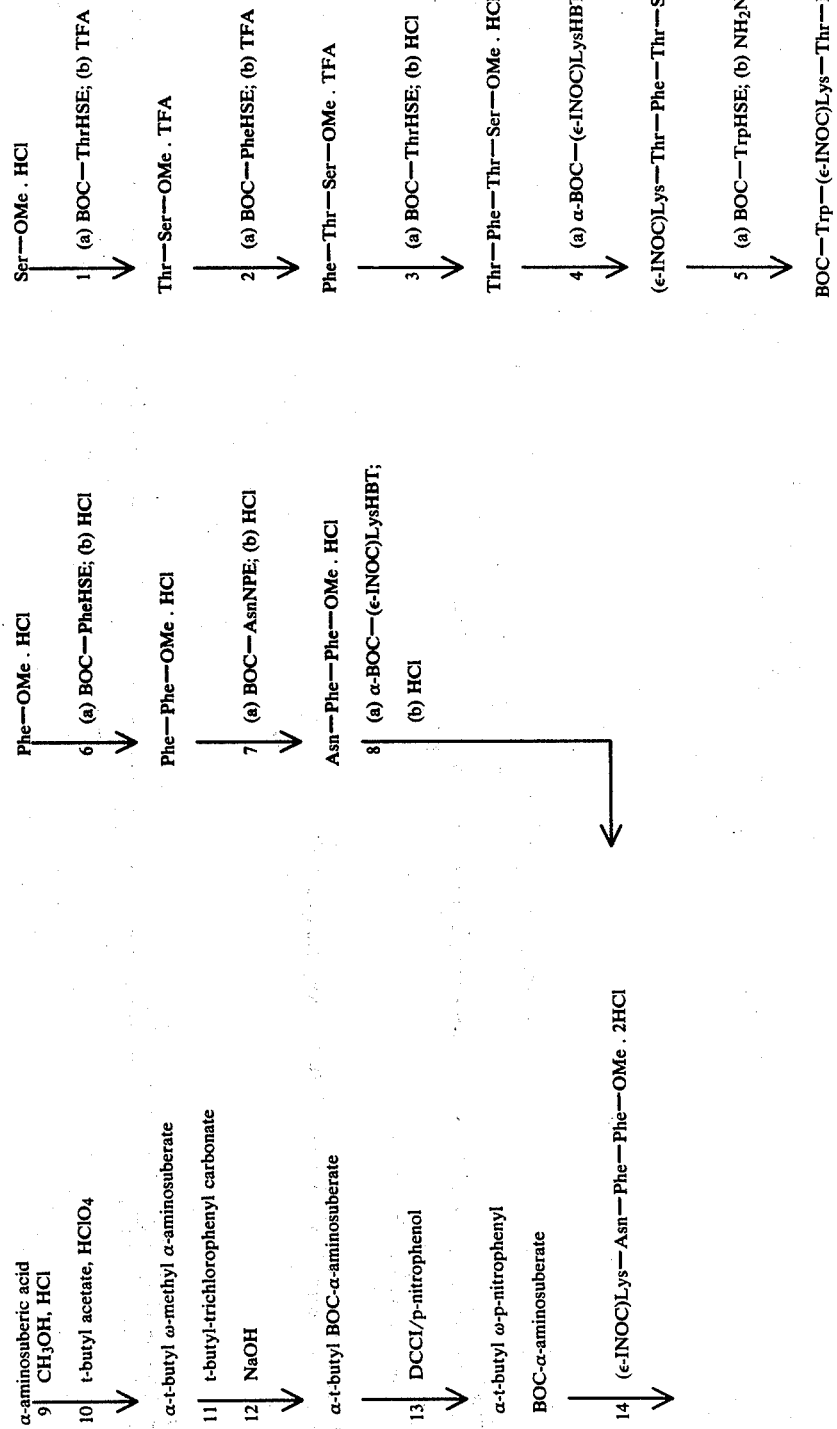

TABLE 3-continued
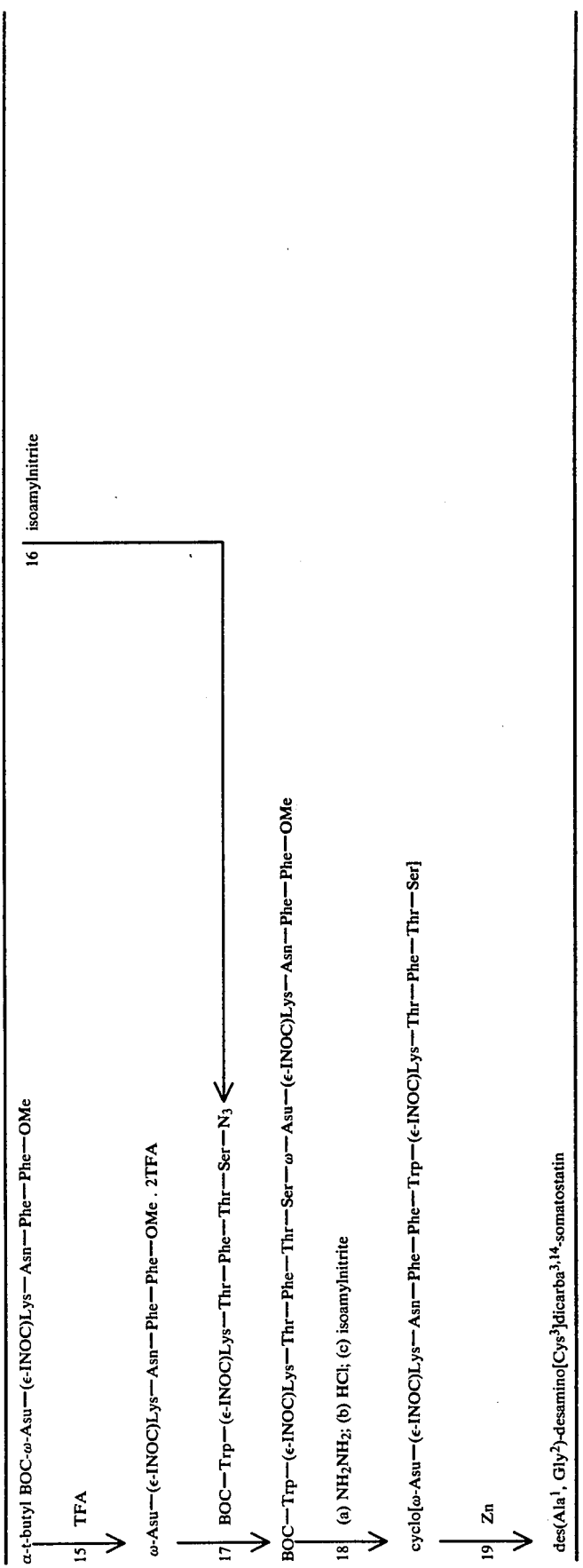

In Table 3 the number appearing to the left of each arrow refers to the illustrative Example which sets forth the experimental details for the indicated conversion.

This preferred overall procedure involves combinations of sequential and block synthesis, wherein certain peptide segments of des(Ala[1], Gly[2])-desamino[Cys[3]]dicarba[3,14]-somatostatin and des(Ala[1], Gly[2])-desamino[Cys[3]]dicarba[3,14]-[D-Trp[8]]-somatostatin are initially formed by the stepwise method, by sequential synthesis in solution, and these segments are then coupled in proper sequence and the two ends of the peptide joined to form the desired cyclic peptide. In this procedure, the BOC substituent is used to protect α-amino groups, the isonicotinyloxycarbonyl group, INOC, is used to protect the ε-amino group of lysine and the methyl ester group is used to protect the carboxyl group of phenylalanine, phenylalanyl-phenylalanine, asparaginyl-phenylalanyl-phenylalanine, (ε-INOC)lysyl-asparaginyl-phenylalanyl-phenylalanine and α-t-butyl ester-BOC-ω-Asu-(ε-INOC)lysyl-asparaginyl-phenylalanyl-phenylalanine. In the case of α-t-butyl ester-BOC-ω-Asu-(ε-INOC)lysyl-asparaginyl-phenylalanyl-phenylalanine-OMe, the methyl ester serves the further purpose of providing the intermediate for preparing, via the hydrazide, Trp-(ε-INOC)Lys-Thr-Phe-Thr-Ser-ω-Asu-(ε-INOC)lysyl-asparaginyl-phenylalanyl-phenylalanine azide or D-Trp-(ε-INOC)Lys-Thr-Phe-Thr-Ser-ω-Asu-(ε-INOC)lysyl-asparaginyl-phenylalanyl-phenylalanine azide. Instead of this preferred method, however, the present invention also contemplates the various permutations of alternate routes, and employment of other protecting groupings fulfilling criteria hereinabove discussed, such alternate routes likewise involving sequential synthesis in solution, and combinations of sequential and block synthesis procedures.

As reference to Table 3 shows, one preferred overall procedure for preparing des(Ala[1], Gly[2])-desamino[Cys[3]]dicarba[3,14]-somatostatin or des(Ala[1], Gly[2])-desamino [Cys[3]]dicarba[3,14]-[D-Trp[8]]-somatostatin specifically involves (a) sequential synthesis of the N-terminal hexapeptide segment, BOC-Trp-(ε-INOC)Lys-Thr-Phe-Thr-Ser-azide and BOC-D-Trp(ε-INOC)Lys-Thr-Phe-Thr-Ser-azide, and (b) the C-terminal pentapeptide segment, ω-Asu-(ε-INOC)Lys-Asn-Phe-Phe-OMe, (c) condensing the peptides prepared in steps (a) and (b) to form the peptide BOC-Trp-(ε-INOC)Lys-Thr-Phe-Thr-Ser-ω-Asu-(ε-INOC)Lys-Asn-Phe-Phe-OMe or BOC-D-Trp(ε-INOC)Lys-Thr-Phe-Thr-Ser-ω-Asu-(ε-INOC)Lys-Asn-Phe-Phe-OMe (d) converting the -OMe to a hydrazide, removing the BOC protective group and, (f) cyclizing and unblocking the resulting undecapeptide to obtain the novel somatostatin analog des(Ala[1], Gly[2])-desamino[Cys[3]]dicarba[3,14]-somatostatin or des(Ala[1], Gly[2])-desamino[Cys[3]]dicarba[3,14]-[D-Trp[8]]-somatostatin.

The N-terminal hexapeptide segment is prepared by reacting Ser-OH.HCl with BOC-ThrHSE. The Ser-OMe hydrochloride is converted to the free amine with a weak base and reacted with BOC-ThrHSE in a suitable organic solvent. The reaction is conducted by bringing the solutions together and stirring at room temperature at approximately neutral pH but preferably at a pH of 6.8 to 8, under which conditions the reaction is ordinarily complete in about four hours. The product is extracted into water and the aqueous solution is evaporated to dryness. The residue is dissolved in a suitable organic solvent and the insoluble salt removed by filtration. The crude product is purified by chromatography to give substantially pure BOC-Thr-Ser-OMe. This dipeptide is treated with TFA, thereby cleaving the BOC substituent to form Thr-Ser-OMe.TFA.

The dipeptide, Thr-Ser-OMe.TFA, is converted to the free amine with a weak base and reacted with a slurry of BOC-PheHSE in a suitable organic solvent, which reaction is conducted by vigorously agitating the reactants together from two hours to overnight at room temperature. The reaction solution is washed with water and the organic layer evaporated to dryness. The resulting crude product is purified by chromatography to give substantially pure BOC-Phe-Thr-Ser-OMe. This tripeptide is treated with TFA to yield substantially pure tripeptide Phe-Thr-Ser-OMe.TFA.

The tripeptide, Phe-Thr-Ser-OMe.TFA is converted to the free base with a weak base and reacted with BOC-ThrHSE in a suitable organic solvent, which reaction is conducted by vigorously agitating the reactants together from about one hour to overnight at room temperature. The precipitate of crude product is collected and reprecipitated from methanol-ether to give substantially pure tetrapeptide, BOC-Thr-Phe-Thr-Ser-OMe. This tetrapeptide is treated with anhydrous hydrogen chloride in ethyl acetate, thereby cleaving the BOC substituent to form Thr-Phe-Thr-Ser-OMe hydrochloride.

α-BOC-(ε-INOC)Lys-OH is reacted with N-hydroxybenzotriazole monohydrate in the presence of DCCI. The resulting α-BOC-(ε-INOC)LysHBT is reacted with the tetrapeptide Thr-Phe-Thr-Ser-OMe hydrochloride which reaction is conducted by contacting the reactants together in a suitable organic solvent, such as freshly degassed DMF/methylene chloride for about one hour to overnight. The insolubles are filtered out and the filtrate evaporated to a small volume. The product is precipitated by the addition of petroleum ether. The crude product is purified by chromatography to give substantially pure blocked pentapeptide α-BOC-(ε-INOC)Lys-Thr-Phe-Thr-Ser-OMe. The blocked pentapeptide is treated with TFA, thereby cleaving the BOC substituent to form the pentapeptide (ε-INOC)Lys-Thr-Phe-Thr-Ser-OMe.2TFA.

The pentapeptide (ε-INOC)Lys-Thr-Phe-Thr-Ser-OMe.2TFA is converted to a free base with a weak base and reacted with BOC-TrpHSE or BOC-D-TrpHSE in a suitable organic solvent, such as DMF, at about a neutral pH, preferably at about 7.5 to about 7.1, under which conditions the reaction is complete after stirring overnight. The product is precipitated by the addition of ether. The crude product is chromatographed to give substantially pure blocked hexapeptide BOC-Trp-(ε-INOC)Lys-Thr-Phe-Thr-Ser-OMe or BOC-D-Trp-(ε-INOC)Lys-Thr-Phe-Thr-Ser-OMe. The blocked hexapeptide is treated with anhydrous hydrazine in methanol to give substantially pure BOC-Trp-(ε-INOC)Lys-Thr-Phe-Thr-Ser-hydrazide or BOC-D-Trp-(ε-INOC)Lys-Thr-Phe-Thr-Ser-hydrazide.

The C-terminal tetrapeptide (ε-INOC)Lys-Asn-Phe-Phe-OMe.2HCl is prepared by reacting Phe-OMe hydrochloride with BOC-PheHSE, which reaction is conducted in a suitable organic solvent, such as chloroform or methylene chloride, overnight at a basic pH. Insoluble materials are separated and the organic solution evaporated to dryness and the residue recrystallized. The blocked dipeptide is treated with anhydrous hydrogen chloride in ethyl acetate, thereby cleaving the BOC substituent to form Phe-Phe-OMe hydrochloride.

The dipeptide Phe-Phe-OMe hydrochloride is reacted with BOC-AsnNPE in a suitable organic solvent such as DMF at neutral pH preferably at about a pH of 7.2 overnight. The reaction solution is concentrated and the residue dissolved in chloroform. The organic solution is washed and evaporated to dryness. The residue is recrystallized to give substantially pure BOC-Asn-Phe-Phe-OMe. The blocked tripeptide is treated with anhydrous hydrogen chloride in ethyl acetate, thereby cleaving the BOC substituent to form Asn-Phe-Phe-OMe hydrochloride.

α-BOC-(ε-INOC)Lys is reacted with 1-hydroxybenzotriazole, HBT, in the presence of DCCI in a suitable organic solvent such as DMF to form α-BOC-(ε-INOC)LysHBT. To this solution is added Asn-Phe-Phe-OMe hydrochloride. The pH of the reaction is adjusted to about neutral and stirred overnight. The reaction mixture is filtered to remove dicyclohexylurea and evaporated to dryness. The residue is suspended in a suitable organic solvent and collected by filtration. The blocked tetrapeptide is treated with anhydrous hydrogen chloride in ethyl acetate, thereby cleaving the BOC substituent to form (ε-INOC)Lys-Asn-Phe-Phe-OMe dihydrochloride.

α-t-Butyl-ω-p-nitrophenyl ester-BOC-α-aminosuberate is formed by treating α-aminosuberic acid with a methanolic solution of anhydrous HCl at 25° C. for 30 minutes to obtain ω-methyl-α-aminosuberate.HCl. The ω-methyl-α-aminosuberate.HCl is treated with perchloric acid in t-butyl acetate. The reaction solution is extracted at neutral pH with an organic solvent to obtain α-t-butyl-ω-methyl-α-aminosuberate.

The α-amino group of α-t-butyl-ω-methyl-α-aminosuberate is protected by conversion to the BOC derivative by reaction with t-butyl-trichlorophenyl carbonate. The reaction is carried out in a suitable organic solvent, such as DMF, at a slightly basic pH of about 8 to 9 and preferably at pH 8.5, overnight at 25° C. The reaction solution is evaporated to dryness, dissolved in a minimum amount of a suitable organic solvent and washed with dilute acid and base. The organic solvent is evaporated to yield substantially pure α-t-butyl ω-methyl N-BOC-α-aminosuberate.

The ω-methyl ester group of α-t-butyl ω-methyl N-BOC-α-aminosuberate is selectively hydrolyzed by treatment with 1.0 N sodium hydroxide in dioxane for 1¼ hours at 25° C. After the organic solvent is evaporated, the remaining solution is acidified and extracted with a suitable organic solvent. The solvent is evaporated and the crude product purified by chromatography to yield pure α-t-butyl BOC-α-aminosuberate.

The ω-carboxylic acid group of α-t-butyl BOC-α-aminosuberate is converted to an active ester group by reaction with p-nitrophenol in the presence of DCCI. After removing solids by filtration, the filtrate is concentrated to a small volume and the desired α-t-butyl ω-p-nitrophenyl BOC-α-aminosuberate is obtained as an oil.

A solution of (ε-INOC)Lys-Asn-Phe-Phe-OMe dihydrochloride is treated with α-t-butyl ω-p-nitrophenyl α-aminosuberate at a basic pH preferably at about pH 8 overnight. The reaction solution is evaporated and the residue purified by chromatography to give substantially pure pentapeptide, α-t-butyl BOC-ω-Asu-(ε-INOC)Lys-Asn-Phe-Phe-OMe. This blocked pentapeptide is treated with TFA to remove both the α-N-BOC and α-t-butyl groups to yield ω-Asu-(ε-INOC)Lys-Asn-Phe-Phe-OMe.2TFA.

A solution of the pentapeptide ω-Asu-(ε-INOC)-Lys-Asn-Phe-Phe-OMe.2TFA is treated with a cold solution of BOC-Trp-(ε-INOC)Lys-Thr-Phe-Thr-Ser-N₃ or BOC-D-Trp-(ε-INOC)Lys-Thr-Phe-Thr-Ser-N₃ freshly prepared by treating BOC-Trp-(ε-INOC)Lys-Thr-Phe-Thr-Ser-NHNH₂ or BOC-D-Trp-(ε-INOC)Lys-Thr-Phe-Thr-Ser-NHNH₂ with isoamylnitrite at −25° C. to give the novel blocked undecapeptide BOC-Trp-(ε-INOC)Lys-Thr-Phe-Thr-Ser-ω-Asu-(ε-INOC)Lys-Asn-Phe-Phe-OMe or BOC-D-Trp-(ε-INOC)-Lys-Thr-Phe-Thr-Ser-ω-Asu-(ε-INOC)Lys-Asn-Phe-Phe-OMe.

The undecapeptide BOC-Trp-(ε-INOC)Lys-Thr-Phe-Thr-Ser-ω-Asu-(ε-INOC)Lys-Asn-Phe-Phe-OMe or BOC-D-Trp-(ε-INOC)Lys-Thr-Phe-Thr-Ser-ω-Asu-(ε-INOC)Lys-Asn-Phe-Phe-OMe is cyclized by forming a peptide bond between the carboxyl group of phenylalanine and the α-amino group of L-tryptophan or D-tryptophan. This is accomplished by (a) converting the -OMe group to a hydrazide by treatment with a methanolic solution of hydrazine; (b) removing the BOC protecting group from L-tryptophan or D-tryptophan by treating the undecapeptide hydrazide with anhydrous HCl in the presence of mercaptoethanol to yield Trp-(ε-INOC)Lys-Thr-Phe-Thr-Ser-ω-Asu-(ε-INOC)Lys-Asn-Phe-Phe-hydrazide.4HCl or D-Trp-(ε-INOC)Lys-Thr-PHe-Thr-Ser-ω-Asu-(ε-INOC)Lys-Asn-Phe-PHe-hydrazide.4HCl having the structure:

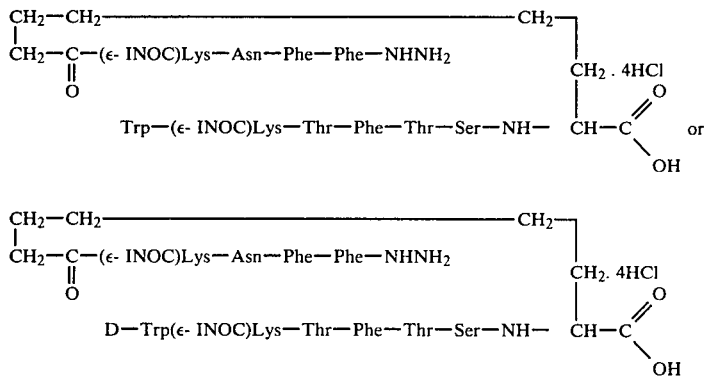

(c) forming the desired cyclic peptide by converting the hydrazide group to an azide by treatment with isoamylnitrite at −25° C. at strongly acid pH; diluting the solution to a concentration of about 1 mg./ml. with a suitable organic solvent in order to favor the cyclization reaction over the polymerization reaction; adjusting the pH to slightly basic to convert the α-amine group of the L-tryptophan or D-tryptophan amino acid to the free α-amino group and initiate the cyclization. The cyclization is completed by allowing the reaction to stand at −20° C. for about four days.

The solvent is evaporated and the residue is reprecipitated from methanol-ethyl acetate to yield substantially pure protected cyclic undecapeptide, cyclo[ω-Asu-(ε-INOC)Lys-Asn-Phe-Phe-Trp-(ε-INOC)Lys-Thr-Phe-Thr-Ser] or cyclo[ω-Asu-(ε-INOC)Lys-Asn-Phe-Phe-D-Trp-(ε-INOC)Lys-Thr-Phe-Thr-Ser].

This blocked undecapeptide is treated with freshly-activated zinc dust in 50% aqueous acetic acid, thereby cleaving the —INOC substituents from the lysine amino acids. The mixture is filtered to remove unreacted Zn and the crude product in the filtrate is purified by chromatography to yield the novel somatostatin analog, des(Ala$^1$, Gly$^2$)-desamino[Cys$^3$]dicarba$^{3,14}$-somatostatin or des(Ala$^1$, Gly$^2$)-desamino[Cys$^3$]dicarba$^{3,14}$-[D-Trp$^8$]-somatostatin in substantially pure form.

Other novel somatostatin analogs of the present invention can be prepared by the process described above with the exception that α-aminosuberic acid is replaced by an equivalent amount of a compound having the structure:

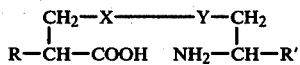

wherein X, Y, R and R' are as defined above.

The following examples illustrate methods of carrying out the present invention, but it is to be understood that these examples are given for purposes of illustration and not of limitation. Furthermore, it is to be understood that wherever L-tryptophan is specified in the following Examples, it can be replaced by D-tryptophan.

EXAMPLE 1

Preparation of Thr-Ser-OMe.TFA

Step a

A mixture of 3.50 g. of Ser-OMe.HCl and 7.47 g. of BOC-ThrHSE in 70 ml. of methylene chloride is stirred together in a 250 ml. round bottom flask. The pH of the solution is adjusted to 7 by the addition of triethylamine and the reaction is allowed to stir for 1½ hours. The reaction mixture is extracted three times with 75 ml. aliquots of water. The aqueous extracts, containing the product, are combined and reextracted once with 45 ml. of methylene chloride and lyophilized to give 14.2 g. of crude product. The crude product is dissolved in 200 ml. of 10% methanol in ether and the solution is filtered to remove salt. The crude product so obtained is applied on a column of 725 g. of Silica Gel-60 and eluted with a mixture of chloroform:methanol:water (80:20:2). The fractions containing product, as identified by thin layer chromatography, are combined and evaporated to dryness. The residue is dissolved in water and lyophilized to give 6.2 g. of BOC-Thr-Ser-OMe.

Step b

BOC-Thr-Ser-OMe, 5.9 g., is suspended in 55 ml. of trifluoroacetic acid at 0° C. After stirring for ten minutes at room temperature, the solid dissolves. After stirring for an additional three minutes, the solution is cooled in an ice bath and 230 ml. each of ether and cold petroleum ether is added to precipitate the product. The solid is isolated by filtration and washed with a 50:50 mixture of ether:petroleum ether and dried in vacuo overnight to give 6.2 g. of Thr-Ser-OMe.TFA.

EXAMPLE 2

Preparation of Phe-Thr-Ser-OMe.TFA

Step a

Thr-Ser-OMe.TFA, 6.2 g., and BOC-Phe-HSE, 6.7 g., are suspended in 100 ml. of methylene chloride. The reaction solution is adjusted to pH 7 by the addition of triethylamine. The reaction mixture is stirred for two hours at 25° C. and is then extracted with water (3×100 ml.). The precipitated crude product is isolated by filtration. The combined water solutions are reextracted with 100 ml. of methylene chloride and the organic solutions combined, dried over magnesium sulfate, filtered and evaporated to dryness to give additional crude product. The combined crude material, 7.9 g., are dissolved in a minimum volume of chloroform:isopropanol (95:5) and applied on a column of 1200 g. of Silica Gel-60. The column is eluted with chloroform:isopropanol (95:5) until no further product is eluted. The column is then eluted with a mixture of chloroform:methanol:water (90:10:1) to elute the product, which is identified by thin layer chromatography. The fractions containing product are combined and evaporated to dryness to give 6.73 g. of BOC-Phe-Thr-Ser-OMe.

Step b

BOC-Phe-Thr-Ser-OMe, 6.63 g., is suspended in 67 ml. of trifluoroacetic acid. The mixture is stirred at 25° C. until solution is complete. The solution is cooled to 0° C. and the product precipitated by the addition of 300 ml. of ether and 600 ml. of petroleum ether. The product is filtered, washed with ether:petroleum ether and dried in vacuo. The yield of substantially pure Phe-Thr-Ser-OMe.TFA is 6.4 g.

EXAMPLE 3

Preparation of Thr-Phe-Thr-Ser-OMe.TFA

Step a

Phe-Thr-Ser-OMe.TFA, 6.4 g., and BOC-Thr-HSE, 4.6 g., is suspended in 100 ml. of methylene chloride. The reaction mixture is adjusted to a pH of 7 by the addition of triethylamine. After stirring the reaction mixture for 1½ hours at 25° C., the crude product is isolated by filtration. The crude product is partially dissolved in 50 ml. methanol and precipitated by the addition of 450 ml. of ether. The partially purified product is isolated by filtration and this precipation process is repeated four times to give substantially pure BOC-Thr-Phe-Thr-Ser-OMe, 6.04 g.

Step b

BOC-Thr-Phe-Thr-Ser-OMe, 5.93 g., is suspended in 45 ml. of ethyl acetate and the suspension cooled to 0° C. in an ice bath. A vigorous stream of anhydrous hydrogen chloride gas is bubbled in for nine minutes followed by a stream of nitrogen for four minutes. Precipitation of the product is completed by the addition of 170 ml. of ether and 285 ml. of petroleum ether. The product is isolated by filtration, washed with a mixture of ether:petroleum ether and dried in vacuo to give 5.66 g. of Thr-Phe-Thr-Ser-OMe-HCl.

EXAMPLE 4

Preparation of (ε-INOC)Lys-Thr-Phe-Thr-Ser-OME.2TFA

Step a

A mixture of 5.63 g. of Thr-Phe-Thr-Ser-OMe.HCl, 4.27 g. of BOC-(ε-INOC)Lys, 2.57 g. of N-hydroxybenzotriazole monohydrate, 20 ml. of DMF and 30 ml. of methylene chloride are stirred together. A solution of 2.42 g. of dicyclohexylcarbodiimide in 4.8 ml. of methylene chloride is added with stirring. Triethylamine, 3.7 ml., is added in three portions over a period of ½ hour with vigorous stirring. The reaction mixture is filtered to remove the precipitated dicyclohexylurea and the urea is washed with chloroform. The combined filtrates and washings are evaporated to a volume of 20 ml. and the product precipitated by the addition of petroleum ether. The precipitated oil is washed five times by decantation with petroleum ether and suspended in approximately 100 ml. of chloroform. The organic mixture is washed by decantation with three portions of 100 ml. of water. The organic phase is filtered and the solid product washed with ether and dried in vacuo to give 8.62 g. of crude product. The crude product is dissolved in 150 ml. of a mixture of chloroform:isopropanol:water (85:19:1.2) and applied on a column packed with 1.3 kg. of Silica Gel-60. The product is eluted with the same solvent mixture. The fractions containing product, as identified by thin layer chromatography, are combined and evaporated in vacuo to give 6.72 g. of substantially pure BOC-(ε-INOC)Lys-Thr-Phe-Thr-Ser-OMe.

Step b

BOC-(ε-INOC)Lys-Thr-Phe-Thr-Ser-OMe, 6.65 g., is dissolved in 65 ml. of trifluoroacetic acid and stirred for three minutes at 25° C. The solution is cooled in an ice bath and the product precipitated by the addition of 250 ml. of cold ether and 400 ml. of cold petroleum ether. The mixture is filtered and the solid washed with a mixture of ether:petroleum ether and dried in vacuo to give 8.1 g. of substantially pure (ε-INOC)Lys-Thr-Phe-Thr-Ser-OME.2TFA.

EXAMPLE 5

Preparation of BOC-Trp-(ε-INOC)Lys-Thr-Phe-Thr-Ser-Hydrazide

Step a (ε-INOC)Lys-Thr-Phe-Thr-Ser-OMe.2TFA, 8.1 g., is dissolved in a minimum volume of DMF and 2.98 g. of BOC-Trp-HSE is added with stirring. Triethylamine is added to bring the solution to pH 7 and the reaction mixture stirred for 3½ hours at 25° C. Additional triethylamine is added to bring the reaction mixture to pH 7 and the mixture is stirred for 18 hours at 25° C. Triethylamine is again added to bring thE pH to 7 and the reaction stirred an additional three hours at 25° C. at which time the reaction is substantially complete. The product is precipitated by the addition of ether and the solvent is removed by decantation. The oily product is induced to solidify by trituration with ether and isolated by filtration. After drying in vacuo, 8.31 g. of crude product is isolated. The crude product is dissolved in a minimum volume of a mixture of chloroform: methanol:water (85:15:1.5) and applied on a column packed with 1 kg. of Silica Gel-60 and eluted with the same solvent mixture. The fractions containing product, as identified by thin layer chromatography, are combined and evaporated to dryness in vacuo to give 5 g. of substantially pure BOC-Trp(ε-INOC)Lys-Thr-Phe-Thr-Ser-OMe.

Step b

BOC-Trp(ε-INOC)Lys-Thr-Phe-Thr-Ser-OMe, 2 g., is suspended in 3 ml. of a mixture of methanol:hydrazine (2:1) at 0° C. and stirred until the suspension is homogeneous. Anhydrous hydrazine is added dropwise until solution is complete. The reaction solution is stirred an additional 15 minutes at 25° C. and evaporated to dryness in vacuo. The residual solid is flushed in vacuo with methanol (2×5 ml.). The product is suspended in methanol, stirred and separated by centrifugation. The product is washed with 30 ml. methanol and separated by centrifugation five times and dried in vacuo to give 1.6 g. of substantially pure BOC-Trp(ε-INOC)Lys-Thr-Phe-Thr-Ser-hydrazide.

EXAMPLE 5a

Preparation of BOC-D-Trp-(ε-INOC)Lys-Thr-Phe-Thr-Ser-Hydrazide

The title compound is prepared by using the process of Example 5, Steps a and b, wherein the BOC-Trp-HSE is replaced by BOC-D-Trp-HSE.

EXAMPLE 6

Preparation of Phe-Phe-OMe Hydrochloride

Step a

To a suspension of 10.78 g. Phe-OMe hydrochloride in 500 ml. methylene chloride is added 18.0 g. BOC-PheHSE. The pH is adjusted to 9 with triethylamine to give a clear solution. This solution is allowed to stand overnight. Precipitated solids are filtered out and washed with methylene chloride. The methylene chloride filtrate and washings, containing the product, are combined and washed with saturated sodium chloride solution (2×500 ml.); 10% sodium bicarbonate solution (2×500 ml.) and with 0.1 N $H_2SO_4$ (2×250 ml.). The washes are back washed with methylene chloride (1×200 ml.). The combined methylene chloride solutions are dried over anhydrous sodium sulfate, filtered and evaporated to dryness. The residue is recrystallized from methylene chloride-hexane to obtain 9 g. of the blocked dipeptide BOC-Phe-Phe-OMe, m.p. 122.0°–122.5° C.

Calculated foR BOC-Phe-Phe-OMe: C, 67.57; H, 7.09; N, 6.57; Found: C, 67.67; H, 7.37; N, 6.31.

A second crop of crystals is obtained from the filtrates, weight 11 g.

Step b

The blocked dipeptide, 3.0 g., is suspended in 100 ml. ethyl acetate. The suspension is cooled in an ice bath and a stream of anhydrous HCl was bubbled in for 15 minutes. The HCl gas is purged with nitrogen gas. The solid is filtered, washed with ethyl acetate and dried in vacuo at room temperature to yield 2.10 g. of Phe-Phe-OMe hydrochloride.

Calc. for Phe-Phe-OMe.HCl: C, 63.06; H, 6.41; N, 7.74; Found: C, 63.00; H, 6.52; N, 7.66.

EXAMPLE 7

Preparation of Asn-Phe-Phe-OMe Hydrochloride

Step a

Phe-Phe-OMe hydrochloride, 12.30 g., is dissolved in 102 ml. freshly degassed DMF. To this solution is added 12.86 g. (7% excess) of BOC-AsnNPE. The pH of the reaction solution is adjusted to 7.2 by the addition of 4.73 ml. of TEA and the solution is stirred overnight.

The reaction solution is concentrated to dryness in vacuo and the residue taken up in chloroform. The chloroform solution is washed with water, saturated sodium bicarbonate solution, 0.1 M $H_2SO_4$ and water. The chloroform solution is dried over anhydrous magnesium sulfate and concentrated to dryness. The crude solid residue is dissolved in a minimum amount of hot ethanol. On cooling, the product crystallizes from the ethanol solution. The crystalline product is collected by suction filtration, washed with cold ethanol and dried in vacuo to give 9.18 g. of BOC-Asn-Phe-Phe-OMe.

Step b

BOC-Asn-Phe-Phe-OMe, 8.5 g., is slurried in 110 ml. anhydrous ethyl acetate. This slurry is cooled in an ice bath to 0° C. and a vigorous stream of anhydrous HCl gas is bubbled in for 15 minutes during which time a clear solution is obtained. The solution is purged with a stream of nitrogen gas. Upon the addition of 100 ml. of ether to this solution, the product separates as a solid. The solid is collected by suction filtration, washed with ether (3×100 ml.) and dried in vacuo to give 7.27 g. Asn-Phe-Phe-OMe hydrochloride.

EXAMPLE 8

Preparation of (ε-INOC)Lys-Asn-Phe-Phe-OMe Dihydrochloride

Step a

α-BOC-(ε-INOC)Lys, 1.9 g., is dissolved in 50 ml. freshly degassed DMF. To this solution is added 1-hydroxybenzotriazole, 0.675 g. The solution is stirred and cooled in an ice bath. To this cooled solution is added 1.13 g. DCCI. The ice bath is removed and stirring is continued for 30 minutes. To this reaction mixture is added Asn-Phe-Phe-OMe hydrochloride, 2.38 g. The pH of the reaction mixture is adjusted to 7.6 by the addition of 1.92 ml. of TEA and the reaction mixture stirred overnight at room temperature.

The reaction mixture is filtered to remove any solids and the filtrate evaporated to dryness in vacuo. The residue is stirred in 800 ml. chloroform, collected by suction filtration and the gelatinous solid washed with chloroform and dried in vacuo to give 1.8 g. α-BOC-(ε-INOC)Lys-Asn-Phe-Phe-OMe. The filtrate and washings are evaporated to dryness in vacuo and the solid residue resuspended in chloroform. The solid is collected by suction filtration, washed with chloroform and dried in vacuo to give an additional 1.82 g. of product.

Step b

α-BOC-(ε-INOC)Lys-Asn-Phe-Phe-OMe, 1 g., is slurried in 13 ml. anhydrous ethyl acetate. The suspension is stirred and cooled in an ice bath. A vigorous stream of anhydrous HCl gas is bubbled into the suspension for 15 minutes after which the suspension is purged with nitrogen gas for 15 minutes. The solid is collected by suction filtration, washed with ethyl acetate and dried in vacuo. The weight of the material recovered is 1.04 g.

EXAMPLE 9

Preparation of ω-Methyl-α-Aminosuberate.HCl

Methanolic HCl (saturated), 72 ml., is added to a suspension of 22.8 g. of α-aminosuberic acid in 450 ml. of methanol. The reaction is stirred at 25° C. for 30 minutes, at which time complete solution occurs. The reaction solution is evaporated to dryness and the residual solid is flushed by evaporation of methanol three times. The product is crystalized from methanol on the addition of ether, filtered and dried in vacuo at 25° C. The crude product (18 g.) is recrystallized from methanol:ether to give 13 g. of substantially pure ω-methyl-α-aminosuberate.HCl.

EXAMPLE 10

Preparation of α-t-Butyl ω-Methyl α-Aminosuberate

ω-Methyl-α-aminosuberate.HCl, 13 g., is dissolved in a mixture of 811 ml. of t-butyl acetate and 8.65 ml. of perchloric acid and the solution allowed to stand at 25° C. for four days. The reaction solution is extracted with 0.5 N HCl (2×600 ml.). The combined aqueous solutions are adjusted to pH 7 with sodium bicarbonate and extracted with ether (3×700 ml.). The combined ether extracts are dried over anhydrous sodium sulfate, filtered and evaporated to give 5.5 g. of α-t-butyl ω-methyl α-aminosuberate as an oil.

EXAMPLE 11

Preparation of α-t-Butyl ω-Methyl N-BOC-α-Aminosuberate

α-t-Butyl-ω-methyl-α-aminosuberate, 5.5 g., is dissolved in 80 ml. of DMF. t-Butyl-trichlorophenyl carbonate, 6.0 g., is added and the pH adjusted to 8.5 with triethylamine. Additional triethylamine is added over a period of one hour to maintain a pH of 8.5 and the reaction mixture is stirred overnight at 25° C. The reaction mixture is evaporated to a heavy oil in vacuo and dissolved in 600 ml. of ether. The ether solution is extracted three times with 600-ml. portions of saturated sodium bicarbonate solution, three times with 600-ml. portions of 0.1 N $H_2SO_4$, and finally, once with 600 ml of saturated sodium chloride solution. The ether solution is evaporated to dryness to give α-t-butyl ω-methyl N-BOC-α-aminosuberate, 8.6 g., as a heavy oil.

EXAMPLE 12

Preparation of α-t-Butyl BOC-α-Aminosuberate

α-t-Butyl ω-methyl N-BOC-α-aminosuberate, 5 g., is dissolved in a mixture of 208 ml. of dioxane and 133 ml. of 1.0 N sodium hydroxide. The reaction is stirred 1¼ hours at 25° C. and the organic solvent is removed by evaporation in vacuo. After the addition of 150 ml. of water, the solution is brought to a pH of 4.6 by the addition of dilute sulfuric acid and extracted with ether (3×150 ml.). The combined ether extracts are dried over anhydrous sodium sulphate and evaporated in vacuo to a heavy syrup. The crude product, 4.5 g., is dissolved in a minimum volume of methylene chloride and applied on a column packed with 400 g. Silica Gel-60 and the by-products eluted with methylene chloride. When no further by-products are detected in the eluate by means of thin layer chromatography, the eluate is changed to a mixture of methylene chloride:isopropanol (98:2) to elute the product. Those fractions which contain product, as determined by thin layer chromatography, are combined and evaporated to dryness in vacuo. Crystallization from hexane gives 1.5 g. of α-t-butyl ester-BOC-α-aminosuberate, m.p. 72° to 3° C.

EXAMPLE 13

Preparation of α-t-Butyl ω-p-Nitrophenyl BOC-α-Aminosuberate

A mixture of 1.38 g. of α-t-butyl BOC-α-aminosuberate, 0.556 g. of p-nitrophenol, and 0.865 g. of DCCI in 30 ml. of methylene chloride are stirred together for four hours at 25° C. The reaction mixture is filtered to remove precipitated dicyclohexylurea and the urea is washed with methylene chloride. The combined organic solutions, containing the product, are concentrated in vacuo to a heavy oil. This oil is dissolved in 20 ml. of ether, 0.1 ml. of acetic acid is added and the solution stirred for two hours at 25° C. The solution is concentrated to a heavy oil and the residue dried in vacuo to give 1.7 g. of α-t-butyl ω-p-nitrophenyl BOC-α-aminosuberate.

EXAMPLE 14

Preparation of α-t-Butyl Ester-BOC-ω-Asu-(ε-INOC)Lys-Asn-Phe-Phe-OMe

To a solution of 1 g. of (ε-INOC)Lys-Asn-Phe-Phe-OMe.2HCl in 20 ml. of DMF is added a solution of 0.755 g. of α-t-butyl ω-p-nitrophenyl BOC-α-aminosuberate in 3.5 ml. of THF with stirring at 25° C. The solution is adjusted to pH 8 with diisopropylethylamine and stirred at 25° C. for 18 hours. The reaction mixture is concentrated in vacuo to a heavy oil and dissolved in 50 ml. of methylene chloride. The resulting solution is extracted with water followed by saturated sodium bicarbonate solution until all p-nitrophenol is removed. The solution is further washed with one additional portion of water and dried over anhydrous sodium sulfate. After filtration and evaporation to dryness in vacuo, the crude product is dissolved in a minimum amount of a mixture of chloroform:methanol:water (80:20:2) and applied on a column packed with 150 g. of Silica Gel-60. The product is eluted with the same solvent mixture. Those fractions which contain product, as shown by thin layer chromatography, are combined and evaporated to dryness in vacuo to give 0.885 g. of α-t-butyl ester-BOC-ω-Asu-(ε-INOC)Lys-Asn-Phe-Phe-OMe.

EXAMPLE 15

Preparation of ω-Asu-(ε-INOC)Lys-Asn-Phe-Phe-OMe.2TFA

The product of Example 14, 0.855 g. is dissolved in 5 ml. of trifluoroacetic acid and stirred at 25° C. for 1½ hours. The product is precipitated on the addition of petroleum ether and isolated by centrifugation. The resulting solid is washed with petroleum ether (3×10 ml.), separated by centrifugation and dried in vacuo to give 0.725 g. of ω-Asu-(ε-INOC)Lys-Asn-Phe-Phe-OMe.2TFA.

EXAMPLE 16

Preparation of BOC-Trp-(ε-INOC)Lys-Thr-Phe-Thr-Ser-Azide

BOC-Trp-(ε-INOC)Lys-Thr-Phe-Thr-Ser-hydrazide, 0.667 g., prepared by the process described in Example 5, is dissolved in 6.3 ml. of DMF with stirring at −25° C. and 0.585 ml. of 5.5 N HCl in THF is added. Isoamylnitrite, 75 mg., is added in seven portions over a period of two hours with stirring at −25° C. to give a solution of the hexapeptideazide.

EXAMPLE 16a

Preparation of BOC-D-Trp-(ε-INOC)Lys-Thr-Phe-Thr-Ser-Azide

The title compound is prepared by using the process of Example 16, wherein the BOC-Trp-(ε-INOC)Lys-Thr-Phe-Thr-Ser-hydrazide is replaced by BOC-D-Trp-(ε-INOC)Lys-Thr-Phe-Thr-Ser-hydrazide, prepared by the process described in Example 5a.

EXAMPLE 17

Preparation of BOC-Trp-(ε-INOC)Lys-Thr-Phe-Thr-Ser-ω-Asu-(ε-INOC)Lys-Asn-Phe-Phe-OMe To the solution of the hexapeptide azide, prepared by the method of Example 16, is added a solution of 0.554 g. of ω-Asu-(ε-INOC)Lys-Asn-Phe-Phe-OMe.2TFA, prepared by the method of Example 15, in 6 ml. of DMF at −30° C. with stirring. The solution is adjusted to pH 7.8 with diisopropylethylamine and allowed to stand at −20° C. for 18 hours. The reaction mixture is evaporated in vacuo to a heavy oil and triturated with 30 ml. of methanol. The solid product is separated by centrifugation and washed with warm methanol (6×30 ml.) and dried in vacuo to yield 0.855 g. of substantially pure protected undecapeptide, BOC-Trp-(ε-INOC)Lys-Thr-Phe-Thr-Ser-ω-Asu-(ε-INOC)Lys-Asn-Phe-Phe-OMe.

EXAMPLE 17a

Preparation of BOC-D-Trp-(ε-INOC)Lys-Thr-Phe-Thr-Ser-ω-Asu-(ε-INOC)Lys-Asn-Phe-Phe-OMe The title compound is prepared by using the process of Example 17, wherein the hexapeptide azide, BOC-Trp-(ε-INOC)Lys-Thr-Phe-Thr-Ser-azide, is replaced by BOC-D-Trp-(ε-INOC)Lys-Thr-Phe-Thr-Ser-azide, prepared by the process described in Example 16a.

EXAMPLE 18

Preparation of Cyclo[ω-Asu-(ε-INOC)Lys-Asn-Phe-Phe-Trp-(ε-INOC)Lys-Thr-Phe-Thr-Ser]

Step a

The protected undecapeptide methyl ester prepared by the method of Example 17, 0.85 g., is suspended in 1 ml. of a mixture of methanol:hydrazine (2:1) at 0° C. with stirring. Anhydrous hydrazine is added dropwise until complete solution is attained and the solution is stirred for 15 minutes at 25° C. The reaction solution is evaporated to dryness in vacuo and the solid product triturated with methanol. The resulting solid product is separated by centrifugation, washed several times with methanol and dried in vacuo to give 0.8 g. of substantially pure protected undecapeptide hydrazide.

Step b

The protected undecapeptide hydrazide, prepared by the method of Example 18, Step a, 0.8 g., is suspended in a mixture of 8 ml. of ethyl acetate and 0.8 ml. of mercaptoethanol with stirring at 0° C. A vigorous stream of anhydrous HCl is introduced for a period of 25 minutes at 0° C. followed by a vigorous stream of nitrogen. The precipitated product is isolated by filtration, washed with 75 ml. ethyl acetate and dried in vacuo to give 0.85 g. of substantially pure Trp-($\epsilon$-INOC)Lys-Thr-Phe-Thr-Ser-$\omega$-Asu-($\epsilon$-INOC)Lys-Asn-Phe-Phe-hydrazide.4HCl.

Step c

The undecapeptide hydrazide, prepared by the method of Example 18, Step b, 0.425 g., is dissolved in 3 ml. of DMF at −25° C. with stirring and 0.25 ml. of 5 N HCl in THF is added. Isoamylnitrite, 28 mg., is added in six portions over a period of 1½ hours at −25° C. to give a solution of the undecapeptide azide. This solution is transferred to 420 ml. of DMF at −50° C. to give a total concentration of 1 mg./ml. The solution is adjusted to pH 7.6 by the addition of diisopropylethylamine and stored at −20° C. for four days. The solution is concentrated to dryness in vacuo and further dried in vacuo for 18 hours. The resulting oil is dissolved in a minimum amount of methanol, the solid product precipitated by the addition of ethyl acetate is separated by centrifugation. The solid is further washed with ethyl acetate (3×10 ml.) and dried in vacuo to yield 0.272 g. of substantially pure protected cyclic undecapeptide, cyclo[$\omega$-Asu-($\epsilon$-INOC)Lys-Asn-Phe-Phe-Trp-($\epsilon$-INOC)Lys-Thr-Phe-Thr-Ser].

EXAMPLE 18a

Preparation of Cyclo[$\omega$-Asu-($\epsilon$-INOC)Lys-Asn-Phe-Phe-D-Trp-($\epsilon$-INOC)Lys-Thr-Phe-Thr-Ser]

The title compound is prepared by using the process of Example 18, steps a, b and c, wherein the protected undecapeptide methyl ester, BOC-Trp-($\epsilon$-INOC)Lys-Thr-Phe-Thr-Ser-$\omega$-Asu-($\epsilon$-INOC)Lys-Asn-Phe-Phe-OMe, of Step a is replaced by BOC-D-Trp-($\epsilon$-INOC)Lys-Thr-Phe-Thr-Ser-$\omega$-Asu-($\epsilon$-INOC)Lys-Asn-Phe-Phe-OMe, prepared by the process described in Example 17a.

EXAMPLE 19

Preparation of Des(Ala$^1$, Gly$^2$)-desamino[Cys$^3$]dicarba$^{3,14}$-somatostatin The product, prepared by the method of Example 18, Step c, 0.3 g., is dissolved in 3 ml. of 50% aqueous acetic acid. Activated zinc, 300 mg., is added and the mixture vigorously stirred for two hours. The mixture is filtered to remove excess zinc and applied on a column of Sephadex Gel-25 Superfine and eluted with 50% aqueous acetic acid and collecting 10 ml. fractions. The fractions shown to contain product, as determined by thin layer chromatography, are combined, evaporated to dryness, dissolved in water and lyophilized to give 0.157 g. of substantially pure des(Ala$^1$, Gly$^2$)-desamino[Cys$^3$]dicarba$^{3,14}$-somatostatin. The ultraviolet spectrum shows a maximum at 280 nm. Aminoacid analysis after acid hydrolysis gives Lys$_{2.04}$; Asp$_{1.03}$; Thr$_{2.16}$; Ser$_{0.998}$; Phe$_{3.03}$; Trp$_{0.74}$.

EXAMPLE 19a

Preparation of Des(Ala$^1$, Gly$^2$)-desamino[Cys$^3$]dicarba$^{3,14}$-[D-Trp$^8$]-somatostatin The title compound is prepared by using the process of Example 19, wherein the cyclo[$\omega$-Asn-($\epsilon$-INOC)Lys-Asn-Phe-Phe-Trp-($\epsilon$-INOC)Lys-Thr-Phe-Thr-Ser] is replaced by cyclo[$\omega$-Asn-($\epsilon$-INOC)Lys-Asn-Phe-Phe-D-Trp-($\epsilon$-INOC)Lys-Thr-Phe-Thr-Ser], prepared by the process described in Example 18a.

EXAMPLE 20

Preparation of $\alpha'$-t-Butyl N($\alpha$)-CBZ-N($\alpha'$)-BOC-$\alpha,\alpha'$-Diaminosuberate Cbz-Glu-$\alpha$-methylester, 8.0 g., and BOC-Glu-$\alpha$-t-butyl ester, 8.6 g., are dissolved in 240 ml. methanol and 80 ml. pyridine. Sodium, 250 mg. (0.2 equiv.) is added and the solution treated electrolytically at 4.0 A and 100 V with platinum electrodes size 2.5×4 cm., 2 mm. apart for 55 minutes at 23°–28° C. The reaction is carried out in a metal beaker with stirring; cooling is accomplished with a −40° C. dry-ice/isopropanol bath. The pH of the reaction, measured by moist pH paper, changes from 6.8 to 7.2–7.6. The solution is evaporated in vacuo. The residual oil is suspended in 100 ml. chloroform:ethyl acetate (95:5) and filtered to remove the insoluble sodium salt of the starting materials. The filtrate is evaporated to yield 16.77 g. of a dark oil.

The dark oil, containing a three component diaminosuberic acid derivative mixture, is applied on a column packed with 1700 g. Silica Gel-60 in chloroform:ethyl acetate (95:5) and eluted with the same solvent. After collecting a 1200-ml. forerun, 70-ml. fractions are taken every 45 seconds. The three component product is eluted in fractions 125–290 and 7.82 g. of product is obtained after evaporation.

The crude N($\alpha$)-CBZ-N($\alpha'$)-BOC-$\alpha,\alpha'$-diaminosuberic acid-$\alpha$-methyl ester-$\alpha'$-t-butyl ester (7.82 g.) dissolved in 157 ml. dioxane is treated with 78.5 ml. of 1 N NaOH at room temperature for 15 minutes. Acetic acid (4 ml.) is added and the solution is evaporated in vacuo. The residue is dissolved in water and freeze-dried to give 14.28 g. of crude N($\alpha$)-CBZ-N($\alpha'$)-BOC-$\alpha,\alpha'$-diaminosuberic acid $\alpha'$-t-butyl ester. The crude product is suspended in a solution containing 20 ml. methanol, 4 ml. conc. NH$_4$OH and 70 ml. CHCl$_3$ and filtered. The filtrate is evaporated and the residue redissolved in a solution containing 15 ml. methanol, 2 ml. conc. NH$_4$OH and 45 ml. CHCl$_3$. The solution is applied on a column packed with 1500 g. Silica Gel-60 in CHCl$_3$:MeOH:NH$_4$OH (80:20:2) and eluted with the same solvent. After collecting a forerun of 2100 ml., 70 ml. cuts are taken every 30 seconds. The desired product is eluted in fractions 35–82. These fractions are pooled and evaporated to dryness. The residue is suspended in water, acidified with citric acid and the product extracted into ethyl acetate. The ethyl acetate extract is dried and evaporated to dryness to yield 2.17 g. of the desired $\alpha'$-t-butyl N($\alpha$)-CBZ-N($\alpha'$)-BOC-$\alpha,\alpha'$-diaminosuberate.

The $\alpha'$-t-butyl N($\alpha$)-CBZ-N($\alpha'$)-BOC-$\alpha,\alpha'$-diaminosuberate obtained is employed for the preparation of:

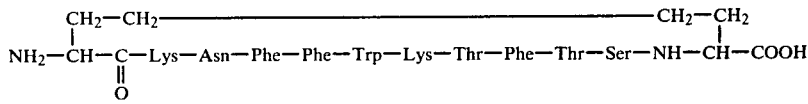

according to the process described in Examples 13 to 15 and 17 to 19; and for the preparation of

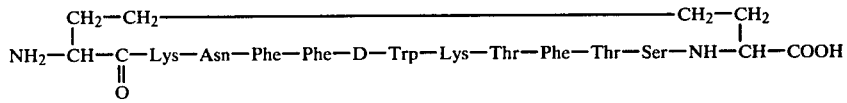

according to the process described in Example 13 to 15 and 17a to 19a.

EXAMPLE 21

Preparation of Des(Ala$^1$,Gly$^2$)-desamino[Cys$^3$]descarboxy[Cys$^{14}$]dicarba$^{3,14}$-[D-Trp$^8$]-somatostatin The title compound is prepared according to the process described in Table 3 wherein the α-aminosuberic acid in the process described in Step 11 is replaced by the compound methyl 7-aminoheptanoate, prepared by the method set forth in C. F. Horn et al., Angew. Chem. 74, 531, (1962); Chemical Abstracts, Vol. 57: 11411(c), and the conversions described in Examples 11 to 15 and 17a, 18a and 19a are carried out. The title compound has R$_f$=0.32 on silica gel thin layer chromatography using ethyl acetate-pyridine-acetic acid-water (10:5:1:3) as solvent.

EXAMPLE 22

Preparation of the Sulfone of Des(Ala$^1$, Gly$^2$)-desamino[Cys$^3$]carba$^3$-somatostatin To a solution of 14 mg. of des(Ala$^1$, Gly$^2$)-desamino[Cys$^3$]carba$^3$-somatostatin and 0.1 mg. of ammonium molybdate in 0.2 ml. of 60% perchloric acid is added 50 μl. of 30% H$_2$O$_2$. The product is purified by passing the solution through a column of Sephadex G-25 using 50% acetic acid as eluent. Elution of the product is detected by tlc using ethylacetate:pyridine:acetic acid:water (10:5:1:3) as a solvent system and those fractions containing product are evaporated to dryness to give the sulfone of des(Ala$^1$, Gly$^2$)-desamino[Cys$^3$]carba$^3$-somatostatin.

EXAMPLE 22a

Preparation of the Sulfone of Des(Ala$^1$, Gly$^2$)-desamino-[Cys$^3$]carba$^3$-[D-Trp$^8$]-somatostatin The title compound is prepared by using the process of Example 22, wherein the des(Ala$^1$, Gly$^2$)desamino-[Cys$^3$]carba$^3$-somatostatin is replaced by des(Ala$^1$, Gly$^2$)-desamino[Cys$^3$]carba$^3$-[D-Trp$^8$]-somatostatin.

EXAMPLE 23

Preparation of the Sulfoxide of Des(Ala$^1$, Gly$^2$)-desamino-[Cys$^3$]carba$^3$-somatostatin To a solution of 14 mg. of des(Ala$^1$, Gly$^2$)-desamino[Cys$^3$]carba$^3$-somatostatin in 0.5 ml. of 0.2 M phosphate buffer at pH 7.0 is added 0.2 ml. of 0.05 M I$_2$ in ethanol and 0.1 ml. of 0.1 M NaOH. The reaction is allowed to stand for five days at 25° C. The product is isolated by passing the solution through a column of Sephadex G-25 using 50% acetic acid as eluent. Elution of the product is detected by tlc using ethylacetate:pyridine:acetic acid:water (10:5:1:3) as a solvent system and those fractions containing product are evaporated to dryness to give the sulfoxide of des(Ala$^1$,Gly$^2$)-desamino[Cys$^3$]carba$^3$-somatostatin.

EXAMPLE 23a

Preparation of the Sulfoxide of Des(Ala$^1$,Gly$^2$)-desamino-[Cys$^3$]carba$^3$-[D-Trp$^8$]-somatostatin The title compound is prepared by using the process of Example 23, wherein the des(Ala$^1$,Gly$^2$)-desamino[Cys$^3$]-carba$^3$-somatostatin is replaced by des(Ala$^1$,Gly$^2$)-desamino-[Cys$^3$]carba$^3$-[D-Trp$^8$]-somatostatin.

It is to be understood that somatostatin analogs of the present invention, containing alanine or α-aminobutyric acid in place of Asn can be prepared by the identical process set forth in Table 1, 2 and 3 wherein the peptide (ε-INOC)Lys-Asn-Phe-Phe-OMe.2HCl is replaced by the peptide (ε-INOC)Lys-Ala-Phe-Phe-OMe.2HCl or (ε-INOC)Lys-[α-aminobutyric acid]-Phe-Phe-OMe.2HCl, respectively. The peptides (ε-INOC)Lys-Ala-Phe-Phe-OMe.2HCl and (ε-INOC)Lys-[α-aminobutyric acid]-Phe-Phe-OMe.2HCl are prepared according to Steps 6, 7 and 8 set forth in Table 3 with the exception that in Step 7(a) BOC-AsnNPE is replaced by BOC-AlaNPE or BOC-[α-aminobutyric acid]NPE, respectively.

As a specific example the somatostatin analog of the present invention, des(Ala$^1$, Gly$^2$)-desamino[Cys$^3$]-descarboxy[Cys$^{14}$]dicarba$^{3,14}$-[Ala$^5$]-somatostatin, is prepared by the process of Table 3 by replacing α-t-butyl BOC-α-aminosuberate with BOC-ω-aminoheptanoic acid in Step 12; and by replacing BOC-AsnNPE with BOC-AlaNPE in Step 7.

As a further specific example, the somatostatin analog of the present invention, des(Ala$^1$, Gly$^2$)-desamino[Cys$^3$]descarboxy[Cys$^{14}$]dicarba$^{3,14}$-[α-aminobutyric acid$^5$]-[D-Trp$^8$]-somatostatin, is prepared by the process of Table 3 by replacing α-t-butyl BOC-α-aminosuberate with BOC-ω-aminoheptanoic acid in Step 12; by replacing BOC-AsnNPE with BOC-[α-aminobutyric acid]NPE in Step 7; and by replacing BOC-TrpHSE with BOC-D-TrpHSE in Step 5a.

The somatostatin analogs of the present invention are useful in humans and animals for inhibiting gastric secretion in the treatment of gastric ulcers, inhibiting growth hormone release as in the treatment of acromegaly, inhibiting the release of glucagon and alone or in conjunction with insulin, for lowering blood glucose as in the treatment of diabetes. In the treatment of diabetes, the number and size of daily doses and the time of administration are determined by an individual study of each subject. The method of determining these factors is known to those skilled in the art.

The somatostatin analogs described herein may be administered to warm blooded animals, including humans, either intravenously, subcutaneously, intramuscularly or orally. The contemplated dose range for oral administration in tablet or capsule form to large mammals is about 0.001 mg. to about 7 mg./kg. of body weight per day. These somatostatin analogs are preferably administered by injection. A therapeutically effective amount of an analog is ordinarily supplied at a dosage level of from about 0.001 mg. to about 2 mg./kg. of body weight. Preferably the range is from about 0.00142 mg. to about 0.428 mg./kg. of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch, and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of des(Ala$^1$, Gly$^2$)-desamino[Cys$^3$]dicarba$^{3,14}$-somatostain suitable for subcutaneous injection.

EXAMPLE 24

| | |
|---|---|
| 1 ml. | sterile saline; |
| 1 mg. | des(Ala$^1$, Gly$^2$)-desamino[Cys$^3$]-dicarba$^{3,14}$-somatostatin. |

What is claimed is:

1. The peptides having the structure:

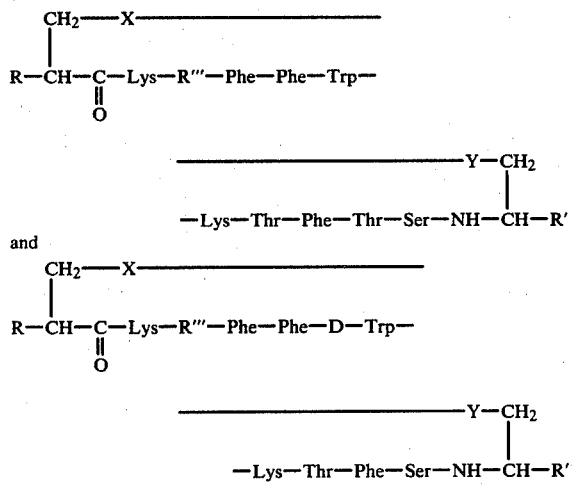

wherein:

X is CH$_2$, S,

SO$_2$ and [X]$_n$ wherein n=0;

Y is CH$_2$, S,

SO$_2$ and [Y]$_n$ wherein n=0;

R is H, NH$_2$ and R"NH and wherein
R" is Ala-Gly-, lower acyl containing 2 to 6 carbon atoms or aroyl containing 7 to 21 carbon atoms;
R' is H and CO$_2$H; wherein X and Y are not both heteroatoms and when R' is H, X and Y are not both —CH$_2$—; and R''' is asparagine, alanine or α-aminobutyric acid.

2. The peptides having the structure:

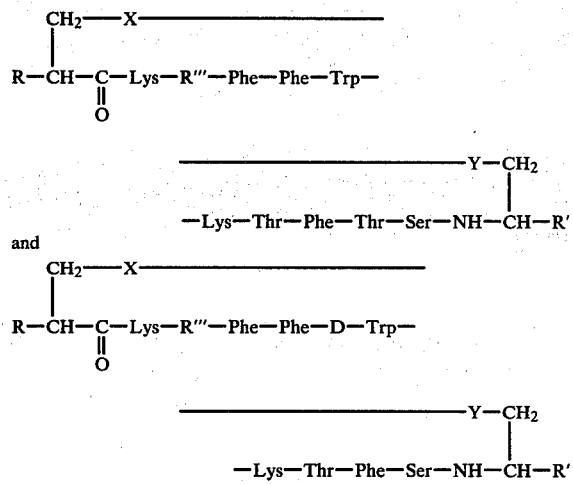

wherein X-Y is:

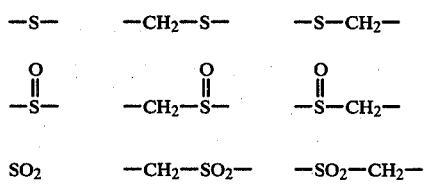

R is H, NH$_2$ and R"NH wherein
R" is Ala-Gly-, lower acyl containing 2 to 6 carbon atoms or aroyl containing 7 to 21 carbon atoms;
R' is H and CO$_2$H and when R' is H, X and Y are also —CH$_2$—CH$_2$— and —CH$_2$—; and R''' is asparagine, alanine or α-aminobutyric acid.

3. The peptide according to claim 2 having the structure:

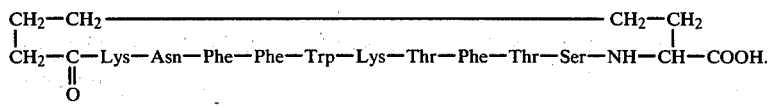

4. The peptide according to claim 3 having the structure:

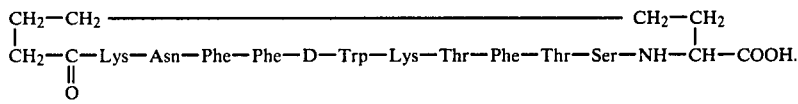

5. The peptide according to claim 2 having the structure:

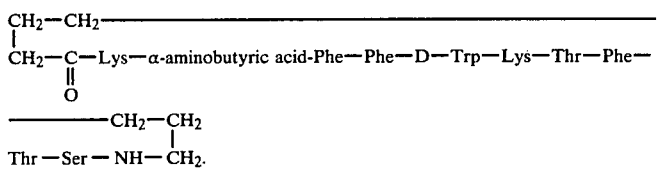

6. The peptide according to claim 2 having the structure:

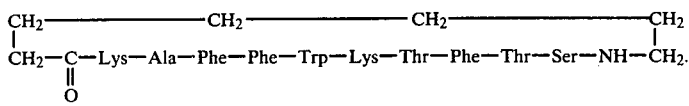

7. The peptide according to claim 2 having the structure:

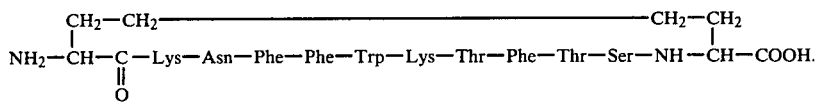

8. The peptide according to claim 7 having the structure:

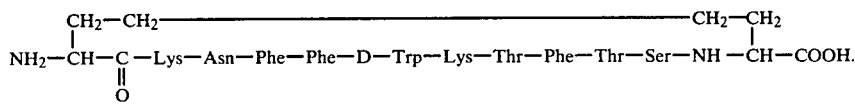

9. The peptide according to claim 2 having the structure:

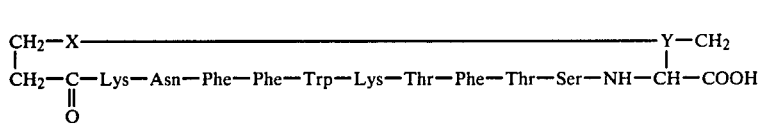

wherein
X-Y is —$CH_2$—S— and —S—$CH_2$—.

10. The peptide according to claim 9 having the structure:

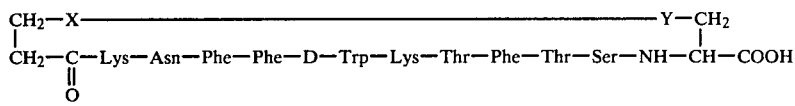

wherein
X-Y is —$CH_2$—S— and —S—$CH_2$—.

11. The peptides having the structure:

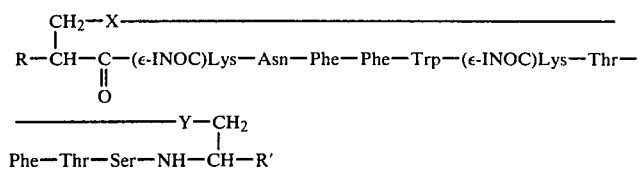

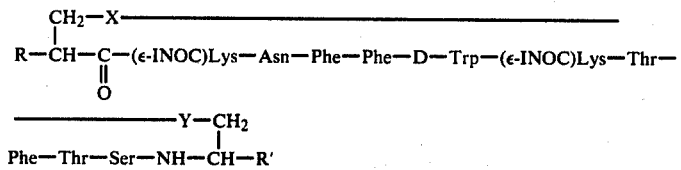

wherein:

X is $CH_2$, S and $[X]_n$ wherein n=0;

Y is $CH_2$, S and $[Y]_n$ wherein n=0;

R is H, $NH_2$ or R"NH wherein

R" is Ala-Gly-, lower acyl containing 1 to 6 carbon atoms or aroyl containing 7 to 21 carbon atoms;

R' is H or $CO_2H$; wherein X and Y are not both heteroatoms.

12. The peptide according to claim 11 having the structure:

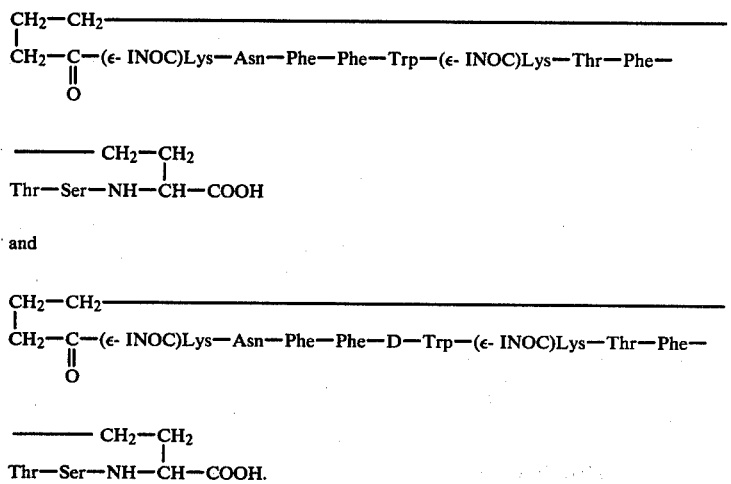

and

13. The peptides having the structure:

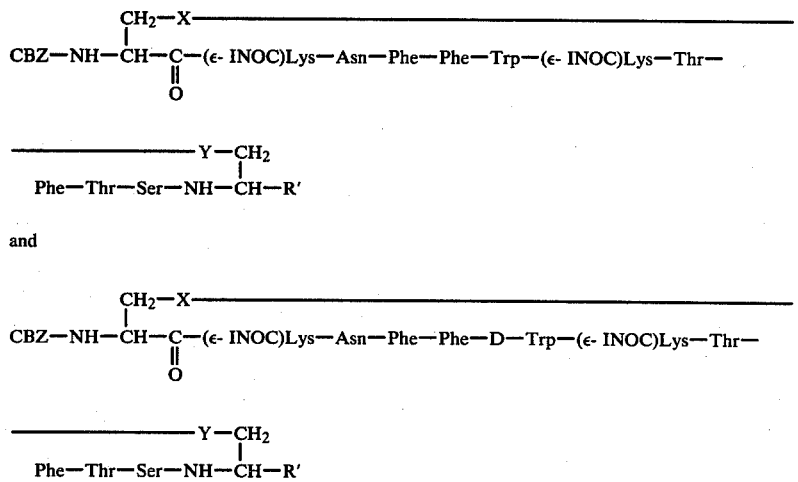

wherein:

X is $CH_2$, S and $[X]_n$ wherein n=0;
Y is $CH_2$, S and $[Y]_n$ wherein n=0;
R' is H and $CO_2H$.

14. The peptides having the structure:

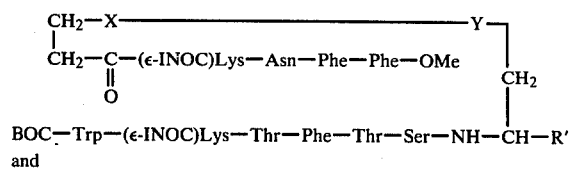

and

-continued

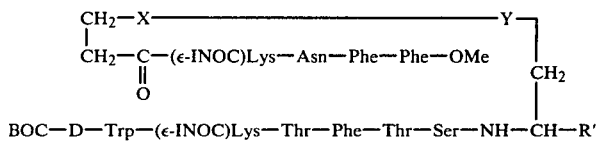

wherein:
X is $CH_2$, S and $[X]_n$ wherein n=0;
Y is $CH_2$, S and $[Y]_n$ wherein n=0;
R' is H and $CO_2H$; wherein X and Y are not both heteroatoms.

15. The peptide according to claim 14 having the structure:

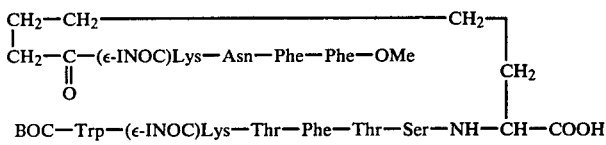

16. The peptide according to claim 15 having the structure:

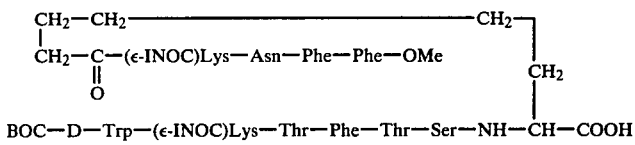

17. The peptides having the structure:

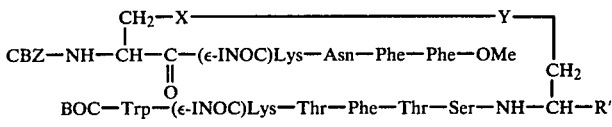

and

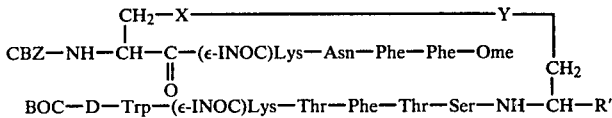

wherein:
X is $CH_2$, S and $[X]_n$ wherein n=0;

Y is $CH_2$, S and $[Y]_n$ wherein n=0;
R' is H and $CO_2H$; wherein X and Y are not both heteroatoms.

18. The peptides having the structure:

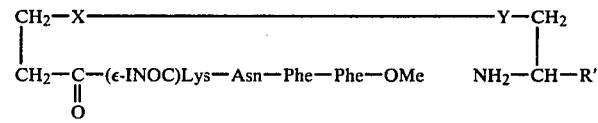

wherein:
X is $CH_2$, S and $[X]_n$ wherein n=0;
Y is $CH_2$, S and $[Y]_n$ wherein n=0;
R' is H or $CO_2H$; wherein X and Y are not both heteroatoms.

19. The peptide according to claim 18 having the structure:

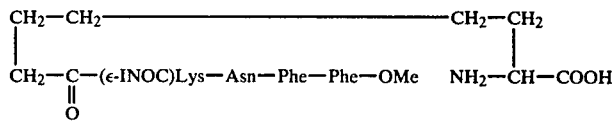

20. The peptides having the structure:

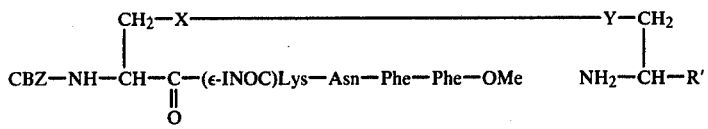

wherein:
X is CH₂, S and [X]ₙ wherein n=0;
Y is CH₂, S and [Y]ₙ wherein n=0;
R' is a H and CO₂H; wherein X and Y are not both heteroatoms.

21. The peptides having the structure:

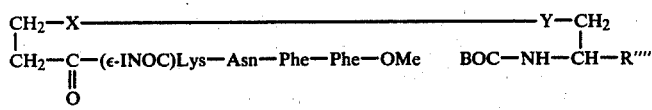

wherein:
X is CH₂, S and [X]ₙ wherein n=0;
Y is CH₂, S and [Y]ₙ wherein n=0;
R'''' is H and —COOtBu; wherein X and Y are not both heteroatoms.

22. The peptides according to claim 21 having the structure:

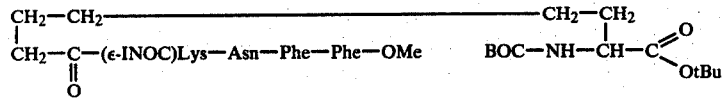

23. The peptides having the structure:

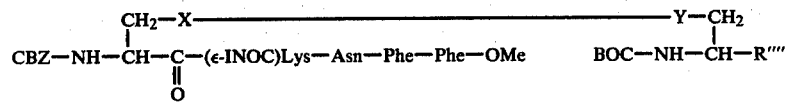

wherein:
X is CH₂, S and [X]ₙ wherein n=0;
Y is CH₂, S and [Y]ₙ wherein n=0;
R'''' is H and —COOtBu; wherein X and Y are not both heteroatoms.

24. The compound having the structure:

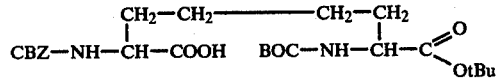

25. The process for preparing the peptides having the structure:

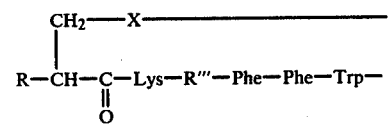

-continued

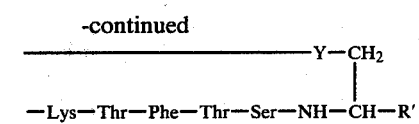

—Lys—Thr—Phe—Thr—Ser—NH—CH—R' and

CH₂—X
|
R—CH—C—Lys—R'''—Phe—Phe—D—Trp—
‖
O

—Lys—Thr—Phe—Ser—NH—CH—R'
                              |
                              Y—CH₂ wherein:
X is CH₂, S, $$\overset{O}{\underset{S,}{\|}}$$

SO₂ and [X]ₙ wherein n=0;
Y is CH₂, S, $$\overset{O}{\underset{S,}{\|}}$$

SO₂ and [Y]ₙ wherein n=0;
R is H, NH₂ and R''NH wherein
R'' is Ala-Gly-, lower acyl containing 2 to 6 carbon atoms or aroyl containing 7 to 21 carbon atoms;
R' is H and CO₂H; wherein X and Y are not both heteroatoms and R''' is asparagine, alanine or α-aminobutyric acid which comprises treating the peptides having the structure:

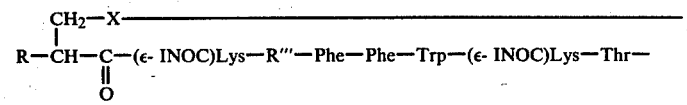

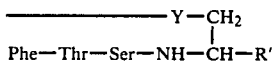

or

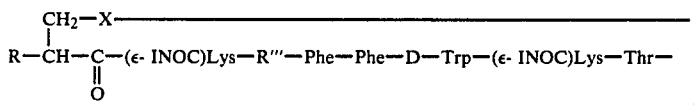

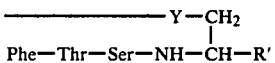

Phe—Thr—Ser—NH—CH—R' wherein X, Y, R, R', R" and R'" are as defined above with zinc dust in an aqueous solution of a lower alkanoic acid and wherein:

X is

and SO₂;

Y is

and SO₂ further oxidizing with performic acid or hydrogen peroxide, respectively.

26. The process according to claim 25 for preparing the peptide having the structure:

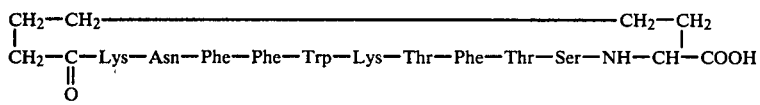

or

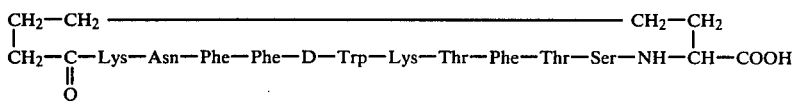

from the peptide of structure:

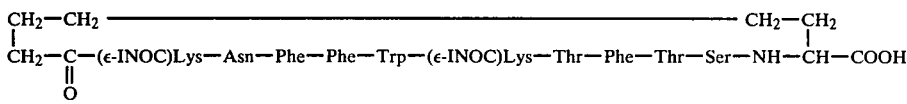

or

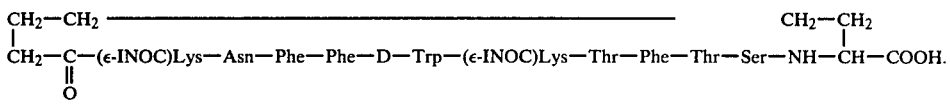

27. The process for preparing the peptides having the structure:

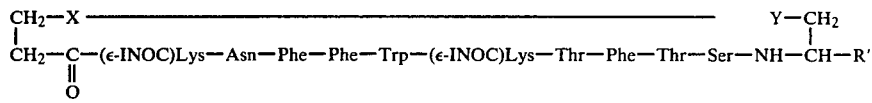

and

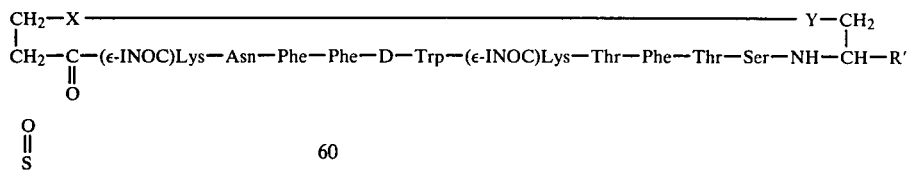

wherein:
X is CH₂, S and [X]ₙ wherein n=0;
Y is CH₂, S and [Y]ₙ wherein n=0;
R' is H and CO₂H; wherein X and Y are not both heteroatoms which comprises treating the peptide of structure:

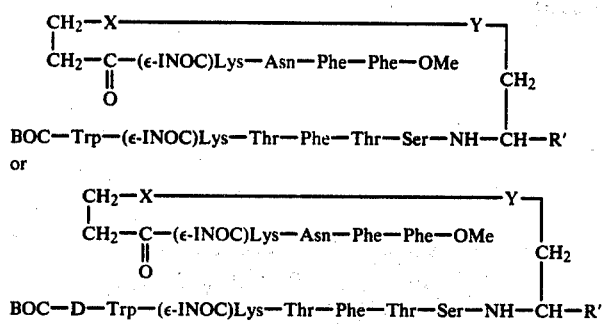

wherein X, Y and R' are as defined above;
(a) with a methanolic solution of hydrazine to convert the -OMe group to a hydrazide;
(b) removing the BOC protecting group from tryptophan by treating the undecapeptide hydrazide with anhydrous HCl in the presence of mercaptoethanol;
(c) forming the desired cyclic peptide by converting the hydrazide group to an azide by treatment with isoamylnitrite at about −25° C. at strongly acid pH; diluting the solution to a concentration of about 1 mg./ml. with a suitable organic solvent;

(d) adjusting the pH to slightly basic to convert the α-amine group of the tryptophan amino acid to the free α-amino group and initiating the cyclization wherein the cyclization is completed by allowing the reaction to stand at about about −20° C. for about four days.

28. The process according to claim 27 for preparing the peptide having the structure:

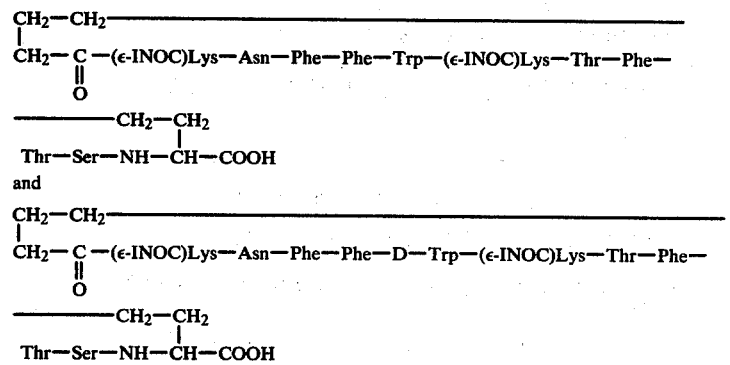

from the peptide having the structure:

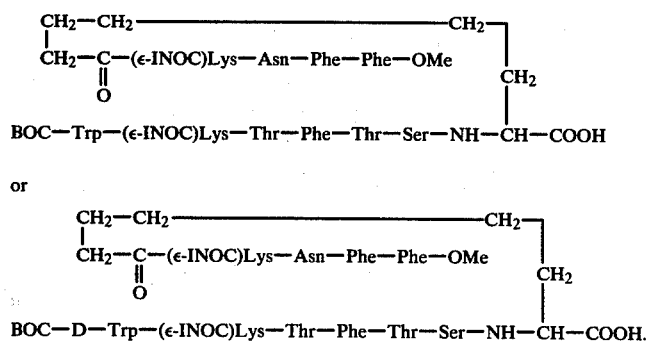

29. The process for preparing the peptides having the structure:

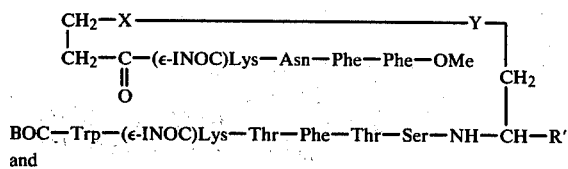

and

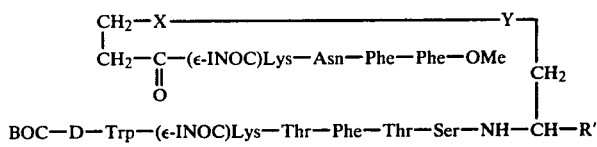

wherein:
X is $CH_2$, S and $[X]_n$ wherein n=0;
Y is $CH_2$, S and $[Y]_n$ wherein n=0;
R' is H and $CO_2H$; wherein X and Y are not both heteroatoms which comprises treating the peptide of structure:

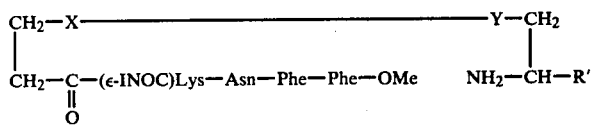

wherein X, Y and R' are as defined above in an inert solvent with a solution of BOC-Trp-(ε-INOC)Lys-Thr-Phe-Thr-Ser-$N_3$ or BOC-D-Trp-(ε-INOC)Lys-Thr-Phe-Thr-Ser-$N_3$ in an inert solvent at about −30° C.

30. The process according to claim 29 for preparing the peptide having the structure:

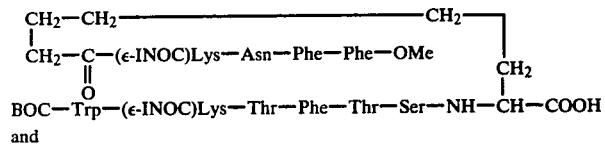

and

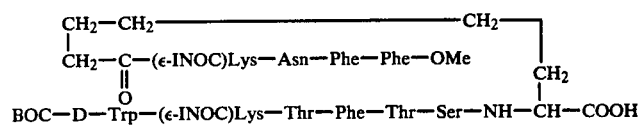

from the peptide having the structure:

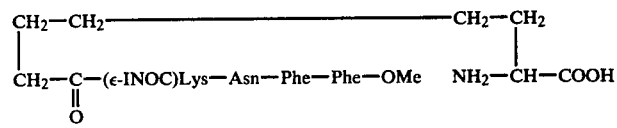

31. The process for preparing the peptides having the structure:

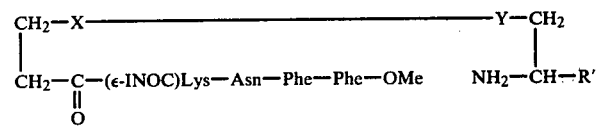

wherein:
X is $CH_2$, S and $[X]_n$ wherein n=0;
Y is $CH_2$, S and $[Y]_n$ wherein n=0;
R' is H and $CO_2H$; wherein X and Y are not both heteroatoms which comprises treating the peptide of structure:

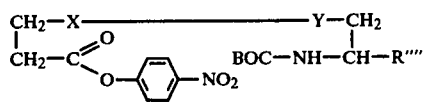

wherein X and Y are as defined above and R'''' is H or

with a solution containing (ε-INOC)Lys-Asn-Phe-Phe-OMe.2HCl at a basic pH for about overnight and treating the resulting blocked pentapeptide with TFA to remove the BOC group.

32. The process according to claim 31 for preparing the peptide having the structure:

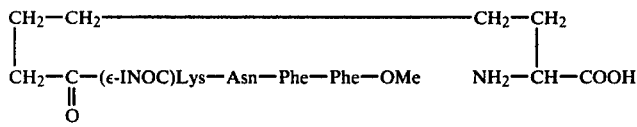

from the peptide having the structure:

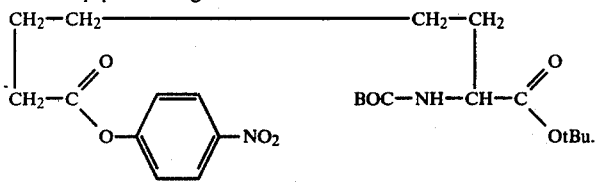

33. A composition comprising a therapeutically effective amount of the peptides having the structure:

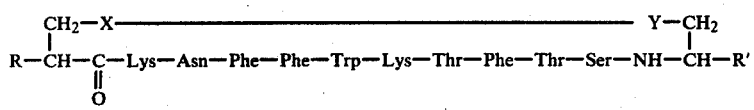

and

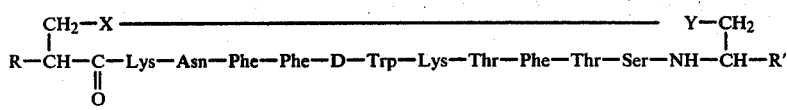

wherein
X is CH$_2$, S,

SO$_2$ and [X]$_n$ wherein n=0;
Y is CH$_2$, S,

SO$_2$ and [Y]$_n$ wherein n=0;
R is H, NH$_2$ and R"NH wherein

R" is Ala-Gly-, lower acyl containing 2 to 6 carbon atoms or aroyl containing 7 to 21 carbon atoms;
R' is H and CO$_2$H; wherein X and Y are not both heteroatoms and when R' is H, X and Y are not both —CH$_2$—; and a pharmaceutically acceptable carrier.

34. A therapeutic composition comprising a therapeutically effective amount of the peptides having the structure:

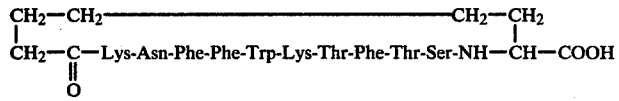

and

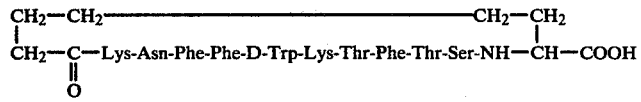

and a pharmaceutically acceptable carrier.

35. A composition according to claim 33 wherein the composition contains from about 0.07 mg. to about 140 mg. of the peptide.

36. A composition according to claim 34 wherein the composition contains from about 0.07 mg. to about 140 mg. of the peptide.

37. A compound of the formula:

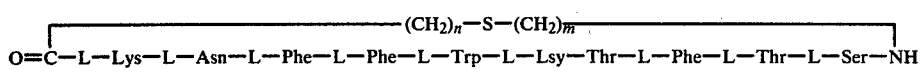

wherein n=2 or 3 and m=2 or 3 with the proviso that n and m are not both 3.

* * * * *